(12) United States Patent
Hunter et al.

(10) Patent No.: US 11,707,363 B2
(45) Date of Patent: Jul. 25, 2023

(54) METHOD AND APPARATUS FOR POST-OPERATIVE TUNING OF A SPINAL IMPLANT

(71) Applicant: Medtronic Navigation, Inc., Louisville, CO (US)

(72) Inventors: Mark W. Hunter, Broomfield, CO (US); Greg Rutz, Boulder, CO (US); Torsten Lyon, Broomfield, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 488 days.

(21) Appl. No.: 15/997,178

(22) Filed: Jun. 4, 2018

(65) Prior Publication Data

US 2018/0280159 A1 Oct. 4, 2018

Related U.S. Application Data

(60) Continuation of application No. 15/868,639, filed on Jan. 11, 2018, which is a division of application No.
(Continued)

(51) Int. Cl.
*A61F 2/46* (2006.01)
*A61B 17/02* (2006.01)
(Continued)

(52) U.S. Cl.
CPC .......... *A61F 2/4657* (2013.01); *A61B 17/025* (2013.01); *A61B 17/15* (2013.01);
(Continued)

(58) Field of Classification Search
None
See application file for complete search history.

(56) References Cited

U.S. PATENT DOCUMENTS

| 1,576,781 A | 3/1926 | Phillips |
| 1,735,726 A | 11/1929 | Bornhardt |

(Continued)

FOREIGN PATENT DOCUMENTS

| CA | 964149 A1 | 3/1975 |
| DE | 3042343 A1 | 6/1982 |

(Continued)

OTHER PUBLICATIONS

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
(Continued)

*Primary Examiner* — Katherine L Fernandez
*Assistant Examiner* — Farouk A Bruce
(74) *Attorney, Agent, or Firm* — Harness, Dickey & Pierce, P.L.C.

(57) ABSTRACT

A tunable implant, system, and method enables a tunable implant to be adjusted within a patient. The tunable implant includes a securing mechanism to secure the implant in the patient, a actuation portion that enables the implant to move and an adjustment portion that permits adjustment of the implant after the implant has been positioned within the patient. The method of adjusting the tunable implant includes analyzing the operation of the implant, determining if any adjustments are necessary and adjusting the implant to improve implant performance. The implant system includes both the tunable implant and a telemetric system that is operable to telemetrically receive data from the tunable implant where the data is used to determine if adjustment of the tunable implant is necessary. The system also includes an instrument assembly that is used for performing spinal surgery where the instrument assembly includes a mounting platform and a jig.

19 Claims, 20 Drawing Sheets

Related U.S. Application Data

10/423,515, filed on Apr. 25, 2003, now Pat. No. 9,867,721, which is a continuation-in-part of application No. 10/354,562, filed on Jan. 30, 2003, now Pat. No. 7,660,623.

(51) Int. Cl.

| | | |
|---|---|---|
| A61B 17/15 | (2006.01) | |
| A61B 17/17 | (2006.01) | |
| A61F 2/44 | (2006.01) | |
| A61B 90/10 | (2016.01) | |
| A61B 34/20 | (2016.01) | |
| A61B 17/00 | (2006.01) | |
| A61F 2/32 | (2006.01) | |
| A61F 2/34 | (2006.01) | |
| A61F 2/36 | (2006.01) | |
| A61F 2/30 | (2006.01) | |
| A61B 90/00 | (2016.01) | |
| A61B 34/10 | (2016.01) | |
| A61B 34/00 | (2016.01) | |
| A61B 34/30 | (2016.01) | |
| A61F 2/48 | (2006.01) | |
| G16Z 99/00 | (2019.01) | |

(52) U.S. Cl.
CPC ........ *A61B 17/1703* (2013.01); *A61B 17/175* (2013.01); *A61B 17/1757* (2013.01); *A61B 34/20* (2016.02); *A61B 90/10* (2016.02); *A61F 2/4425* (2013.01); *G16Z 99/00* (2019.02); *A61B 17/00234* (2013.01); *A61B 34/25* (2016.02); *A61B 34/30* (2016.02); *A61B 2017/00199* (2013.01); *A61B 2017/0256* (2013.01); *A61B 2034/102* (2016.02); *A61B 2034/105* (2016.02); *A61B 2034/107* (2016.02); *A61B 2034/108* (2016.02); *A61B 2034/2051* (2016.02); *A61B 2034/2072* (2016.02); *A61B 2034/252* (2016.02); *A61B 2034/254* (2016.02); *A61B 2034/256* (2016.02); *A61B 2090/363* (2016.02); *A61B 2090/365* (2016.02); *A61B 2090/374* (2016.02); *A61B 2090/376* (2016.02); *A61B 2090/3983* (2016.02); *A61F 2/32* (2013.01); *A61F 2/34* (2013.01); *A61F 2/36* (2013.01); *A61F 2/441* (2013.01); *A61F 2/4607* (2013.01); *A61F 2/4609* (2013.01); *A61F 2/48* (2021.08); *A61F 2002/305* (2013.01); *A61F 2002/3067* (2013.01); *A61F 2002/3069* (2013.01); *A61F 2002/30471* (2013.01); *A61F 2002/30476* (2013.01); *A61F 2002/30517* (2013.01); *A61F 2002/30538* (2013.01); *A61F 2002/30548* (2013.01); *A61F 2002/30565* (2013.01); *A61F 2002/30578* (2013.01); *A61F 2002/30579* (2013.01); *A61F 2002/30586* (2013.01); *A61F 2002/30624* (2013.01); *A61F 2002/30649* (2013.01); *A61F 2002/30668* (2013.01); *A61F 2002/30677* (2013.01); *A61F 2002/449* (2013.01); *A61F 2002/467* (2013.01); *A61F 2002/4632* (2013.01); *A61F 2002/4635* (2013.01); *A61F 2002/4666* (2013.01); *A61F 2002/4668* (2013.01); *A61F 2002/4681* (2013.01); *A61F 2220/0025* (2013.01); *A61F 2220/0091* (2013.01); *A61F 2250/0001* (2013.01); *A61F 2250/0002* (2013.01); *A61F 2250/0006* (2013.01); *A61F 2250/0013* (2013.01); *Y02A 90/10* (2018.01)

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,584,994 A | 4/1986 | Bamberger et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |

(56) References Cited

U.S. PATENT DOCUMENTS

| | | |
|---|---|---|
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |

(56) References Cited

U.S. PATENT DOCUMENTS

| | | |
|---|---|---|
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,403,321 A | 4/1995 | DiMarco |
| 5,408,409 A | 4/1995 | Glassman et al. |
| 5,413,573 A | 5/1995 | Koivukangas |
| 5,415,660 A | 5/1995 | Campbell et al. |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,466,261 A | 11/1995 | Richelsoph |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |

(56) References Cited

U.S. PATENT DOCUMENTS

| | | |
|---|---|---|
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,824,085 A | 10/1998 | Sahay et al. |
| 5,825,908 A | 10/1998 | Pieper et al. |
| 5,828,725 A | 10/1998 | Levinson |
| 5,828,770 A | 10/1998 | Leis et al. |
| 5,829,444 A | 11/1998 | Ferre et al. |
| 5,830,222 A | 11/1998 | Makower |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,899,859 A | 5/1999 | Votruba et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,690 A | 8/1999 | Law et al. |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,957,844 A | 9/1999 | Dekel et al. |
| 5,961,553 A | 10/1999 | Coty et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,408 A | 2/2000 | Bello et al. |
| 6,024,695 A | 2/2000 | Taylor et al. |
| 6,050,724 A | 4/2000 | Schmitz et al. |
| 6,050,963 A | 4/2000 | Johnson et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,144,875 A | 11/2000 | Schweikard et al. |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,190,414 B1 | 2/2001 | Young et al. |
| 6,194,639 B1 | 2/2001 | Botella et al. |
| 6,201,387 B1 | 3/2001 | Govari |
| 6,203,497 B1 | 3/2001 | Dekel et al. |
| 6,205,411 B1 | 3/2001 | DiGioia, III et al. |
| 6,211,666 B1 | 4/2001 | Acker |
| 6,223,067 B1 | 4/2001 | Vilsmeier et al. |
| 6,233,476 B1 | 5/2001 | Strommer et al. |
| 6,245,109 B1 | 6/2001 | Mendes et al. |
| 6,246,231 B1 | 6/2001 | Ashe |
| 6,259,942 B1 | 7/2001 | Westermann et al. |
| 6,264,655 B1 | 7/2001 | Pisharodi |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,332,089 B1 | 12/2001 | Acker et al. |
| 6,332,887 B1 | 12/2001 | Knox |
| 6,341,231 B1 | 1/2002 | Ferre et al. |
| 6,348,058 B1 | 2/2002 | Melkent et al. |
| 6,351,659 B1 | 2/2002 | Vilsmeier |
| 6,375,682 B1 | 4/2002 | Fleischmann et al. |
| 6,381,485 B1 | 4/2002 | Hunter et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,434,507 B1 * | 8/2002 | Clayton ........... A61B 17/32002 600/104 |
| 6,437,567 B1 | 8/2002 | Schenck et al. |
| 6,445,943 B1 | 9/2002 | Ferre et al. |
| 6,466,261 B1 | 10/2002 | Nakamura |

(56) References Cited

U.S. PATENT DOCUMENTS

| | | | |
|---|---|---|---|
| 6,470,207 B1 | 10/2002 | Simon et al. | |
| 6,474,341 B1 | 11/2002 | Hunter et al. | |
| 6,478,802 B2 | 11/2002 | Kienzle, III et al. | |
| 6,484,049 B1 | 11/2002 | Seeley et al. | |
| 6,490,475 B1 | 12/2002 | Seeley et al. | |
| 6,493,573 B1 | 12/2002 | Martinelli et al. | |
| 6,498,944 B1 | 12/2002 | Ben-Haim et al. | |
| 6,499,488 B1 | 12/2002 | Hunter et al. | |
| 6,516,046 B1 | 2/2003 | Frohlich et al. | |
| 6,527,443 B1 | 3/2003 | Vilsmeier et al. | |
| 6,551,325 B2 | 4/2003 | Neubauer et al. | |
| 6,584,174 B2 | 6/2003 | Schubert et al. | |
| 6,609,022 B2 | 8/2003 | Vilsmeier et al. | |
| 6,611,700 B1 | 8/2003 | Vilsmeier et al. | |
| 6,640,128 B2 | 10/2003 | Vilsmeier et al. | |
| 6,694,162 B2 | 2/2004 | Hartlep | |
| 6,701,179 B1 | 3/2004 | Martinelli et al. | |
| 6,895,268 B1 | 5/2005 | Rahn et al. | |
| 6,947,786 B2 | 9/2005 | Simon et al. | |
| 7,660,623 B2 | 2/2010 | Hunter et al. | |
| 7,974,677 B2 | 7/2011 | Mire et al. | |
| 9,867,721 B2 | 1/2018 | Hunter | |
| 2001/0007918 A1 | 7/2001 | Vilsmeier et al. | |
| 2001/0027272 A1* | 10/2001 | Saito | A61B 34/20 600/426 |
| 2001/0053885 A1 | 12/2001 | Gielen et al. | |
| 2002/0049394 A1 | 4/2002 | Roy et al. | |
| 2002/0055741 A1 | 5/2002 | Schlapfer et al. | |
| 2002/0058872 A1* | 5/2002 | Steininger | A61B 8/0833 128/916 |
| 2002/0077540 A1 | 6/2002 | Kienzle | |
| 2002/0077541 A1* | 6/2002 | Kienzle, III | A61B 17/1725 600/424 |
| 2002/0087163 A1 | 7/2002 | Dixon et al. | |
| 2002/0095081 A1 | 7/2002 | Vilsmeier et al. | |
| 2002/0120188 A1* | 8/2002 | Brock | A61B 34/30 600/407 |
| 2002/0151894 A1* | 10/2002 | Melkent | A61B 17/1757 606/86 A |
| 2002/0151978 A1 | 10/2002 | Zacouto et al. | |
| 2003/0023305 A1 | 1/2003 | McKay | |
| 2003/0028196 A1 | 2/2003 | Bonutti | |
| 2003/0032963 A1 | 2/2003 | Reiss et al. | |
| 2003/0069591 A1 | 4/2003 | Carson et al. | |
| 2003/0120150 A1 | 6/2003 | Govari | |
| 2003/0135089 A1 | 7/2003 | Forsell | |
| 2003/0192557 A1* | 10/2003 | Krag | A61B 17/32053 128/898 |
| 2003/0194505 A1 | 10/2003 | Milbocker | |
| 2003/0225331 A1 | 12/2003 | Diederich et al. | |
| 2003/0229348 A1 | 12/2003 | Sevrain | |
| 2004/0024309 A1 | 2/2004 | Ferre et al. | |
| 2004/0092815 A1 | 5/2004 | Schweikard et al. | |
| 2004/0097952 A1 | 5/2004 | Sarin et al. | |
| 2004/0102814 A1 | 5/2004 | Sorensen et al. | |
| 2004/0236424 A1 | 11/2004 | Berez et al. | |
| 2004/0254584 A1 | 12/2004 | Sarin et al. | |
| 2005/0043621 A1 | 2/2005 | Perlin | |
| 2005/0254814 A1 | 11/2005 | Sakamoto | |

FOREIGN PATENT DOCUMENTS

| | | |
|---|---|---|
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 19856013 A1 | 6/2000 |
| DE | 10013519 A1 | 10/2001 |
| DE | 20111479 U1 | 10/2001 |
| DE | 10085137 | 11/2002 |
| DE | 10085137 B4 | 7/2010 |
| EP | 0062941 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 | 5/1991 |
| EP | 0456103 | 11/1991 |
| EP | 0581704 | 2/1994 |
| EP | 0651968 | 5/1995 |
| EP | 0655138 | 5/1995 |
| EP | 0820731 A2 | 1/1998 |
| EP | 0894473 A2 | 2/1999 |
| EP | 0908146 A2 | 4/1999 |
| EP | 0930046 A2 | 7/1999 |
| EP | 1057461 A1 | 12/2000 |
| EP | 1103229 A2 | 5/2001 |
| EP | 1188421 A2 | 3/2002 |
| EP | 1442715 A2 | 8/2004 |
| EP | 1844719 A2 | 10/2007 |
| EP | 1844726 A2 | 10/2007 |
| FR | 2417970 | 9/1979 |
| FR | 2618211 | 1/1989 |
| GB | 1243353 A | 8/1971 |
| GB | 2094590 A | 9/1982 |
| GB | 2164856 A | 4/1986 |
| JP | 62327 | 1/1983 |
| JP | S62-327 A | 1/1987 |
| JP | 2765738 | 6/1988 |
| JP | 63240851 | 10/1988 |
| JP | 2765738 T | 4/1991 |
| JP | 3267054 | 11/1991 |
| JP | 6194639 | 7/1994 |
| WO | 8809151 | 12/1988 |
| WO | 8905123 | 6/1989 |
| WO | 9005494 A1 | 5/1990 |
| WO | 9103982 A1 | 4/1991 |
| WO | 9104711 A1 | 4/1991 |
| WO | 9107726 A1 | 5/1991 |
| WO | 9203090 | 3/1992 |
| WO | 9206645 A1 | 4/1992 |
| WO | 9404938 A1 | 3/1994 |
| WO | 9423647 | 10/1994 |
| WO | 9424933 A1 | 11/1994 |
| WO | 9507055 A1 | 3/1995 |
| WO | 9611624 A2 | 4/1996 |
| WO | 9632059 A1 | 10/1996 |
| WO | 9736192 A1 | 10/1997 |
| WO | 9749453 A1 | 12/1997 |
| WO | 9808554 | 3/1998 |
| WO | 9808554 A1 | 3/1998 |
| WO | 9838908 | 9/1998 |
| WO | 9915097 A2 | 4/1999 |
| WO | 9921498 A1 | 5/1999 |
| WO | 9923956 A1 | 5/1999 |
| WO | 9926549 A1 | 6/1999 |
| WO | 9927839 A2 | 6/1999 |
| WO | 9929253 A1 | 6/1999 |
| WO | 9933406 A1 | 7/1999 |
| WO | 9937208 A1 | 7/1999 |
| WO | 9938449 A1 | 8/1999 |
| WO | 9952094 A1 | 10/1999 |
| WO | 9960939 | 12/1999 |
| WO | 9960939 A1 | 12/1999 |
| WO | 0023015 A1 | 4/2000 |
| WO | 0130437 | 5/2001 |
| WO | 0130437 A1 | 5/2001 |
| WO | 0176497 A1 | 10/2001 |
| WO | 0237935 A2 | 5/2002 |
| WO | 02067783 A2 | 9/2002 |

(56) References Cited

FOREIGN PATENT DOCUMENTS

| WO | 03039377 A1 | 5/2003 |
|---|---|---|
| WO | 03079940 A2 | 10/2003 |

OTHER PUBLICATIONS

Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kall, B., The Impact of Computer and Imaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated).
Kosugi, Y., et al., An Articulated Neurosurgical Navigation System Using MRI and CT Images, IEEE Trans. on Biomed. Eng. vol. 35, No. 2, pp. 147-152 (Feb. 1988).

Krybus, W., et al., Navigation Support for Surgery by Means of Optical Position Detection, Computer Assisted Radiology Proceed, of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al., "Computer Assisted Driving of a Needle into the Brain," Proceedings of the International Symposium CAR '89, Computer Assisted Radiology, 1989, p. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique For Accurate Transpedicular Screw Fixation Using CT Data and a 3-D Optical Localizer," TIMC, Faculte de Medecine de Grenoble.
Lavallee et al., "Image guided operating robot: a clinical application in stereotactic neurosurgery," Proceedings of the 1992 IEEE Internation Conference on Robotics and Automation, May 1992, pp. 618-624.
Lavallee et al., "Matching 3-D Smooth Surfaces with their 2-D Projections using 3-D Distance Maps," SPIE, vol. 1570, Geometric Methods in Computer Vision, 1991, pp. 322-336.
Lavallee et al., "Matching of Medical Images for Computed and Robot Assisted Surgery," IEEE EMBS, Orlando. 1991.
Lavallee, "A New System for Computer Assisted Neurosurgery," IEEE Engineering in Medicine & Biology Society 11th Annual International Conference, 1989, pp. 0926-0927.
Lavallee, "VI Adaption de la Methodologie a Quelques Applications Cliniques," Chapitre VI, pp. 133-148.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.
Mazier et al., Chirurgie de la Colonne Vertebrate Assistee par Ordinateur: Application au Vissage Pediculaire, Innov. Tech. Biol. Med., vol. 11, No. 5, 1990, pp. 559-566.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Merloz, et al., "Computer Assisted Spine Surgery", Clinical Assisted Spine Surgery, No. 337, pp. 86-96.
Ng, W.S et al., Robotic Surgery—A First-Hand Experience in Transurethral Resection of the Prostate Surgery, IEEE Eng. in Med. and Biology, pp. 120-125 (Mar. 1993).
Partial European Search Report for Application No. EP 04 00 1428.

(56) References Cited

OTHER PUBLICATIONS

Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds., 1991).
Pelizzari et al., No. 528—"Three Dimensional Correlation of PET, CT and MRI Images," The Journal of Nuclear Medicine, vol. 28, No. 4, Apr. 1987, p. 682.
Penn, R.D., et al., Stereotactic Surgery with Image Processing of Computerized Tomographic Scans, Neurosurgery, vol. 3, No. 2, pp. 157-163 (Sep.-Oct. 1978).
Phillips et al., "Image Guided Orthopaedic Surgery Design and Analysis," Trans. Inst. MC, vol. 17, No. 5, 1995, pp. 251-264.
Pixsys, 3-D Digitizing Accessories, by Pixsys (marketing brochure)(undated) (2 pages).
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt et al.,"CT-Guided 'Real Time' Stereotaxy," ACTA Neurochirurgica, 1989.
Reinhardt, H., et al., A Computer-Assisted Device for Intraoperative CT-Correlated Localization of Brain Tumors, pp. 51-58 (1988).
Reinhardt, H.F., et al., Mikrochirugische Entfernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).
Reinhardt, H.F., et al., Sonic Stereometry in Microsurgical Procedures for Deep-Seated Brain Tumors and Vascular Malformations, Neurosurgery, vol. 32, No. 1, pp. 51-57 (Jan. 1993).
Reinhardt, Hans. F., Neuronavigation: A Ten-Year Review, Neurosurgery, pp. 329-341 (undated).
Roberts et al., "A frameless stereotaxic integration of computerized tomographic imaging and the operating microscope," J. Neurosurg., vol. 65, Oct. 1986, pp. 545-549.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS Tesions under direct 3-D vision," J. Neurosurg., vol. 52, 1980, pp. 21-27.
Simon, D.A., Accuracy Validation in Image-Guided Orthopaedic Surgery, Second Annual Intl. Symp. on Med. Rob. on Comp-Assisted surgery, MRCAS '95. pp. 185-192 (undated).
Smith et al., "Computer Methods for Improved Diagnostic Image Display Applied to Stereotactic Neurosurgery," Automedical, vol. 14, 1992, pp. 371-382 (4 unnumbered pages).
Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.
Smith, K.R., et al. Multimodality Image Analysis and Display Methods for Improved Tumor Localization in Stereotactic Neurosurgery, Annual Intl. Conf. of the IEEE Eng. in Med. and Biol. Soc., vol. 13, No. 1, p. 210 (1991).
Tan, K., Ph.D., et al., A frameless stereotactic approach to neurosurgical planning based on retrospective patient-image registration, J Neurosurgy, vol. 79, pp. 296-303 (Aug. 1993).
The Laitinen Stereotactic System, E2-E6.
The Partial European Search Report dated Apr. 23, 2008 for European Patent Application No. EP 07 11 1195 has been provided.

Thompson, et al., A System for Anatomical and Functional Mapping of the Human Thalamus, Computers and Biomedical Research, vol. 10, pp. 9-24
Trobraugh, J.W., et al., Frameless Stereotactic Ultrasonography: Method and Applications, Computerized Medical Imaging and Graphics, vol. 18, No. 4, pp. 235-246 (1994).
Viant et al., "A Computer Assisted Orthopaedic System for Distal Locking of Intramedullary Nails," Proc. of MediMEC '95, Bristol, 1995, pp. 86-91.
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Watanabe, E., M.D., et al., Open Surgery Assisted by the Neuronavigator, a Stereotactic, Articulated, Sensitive Arm, Neurosurgery, vol. 28, No. 6, pp. 792-800 (1991).
Weese et al., "An Approach to 2D/3D Registration of a Vertebra in 2D X-ray Fluoroscopies with 3D CT Images," (1997) pp. 119-128.
European Office Action dated Aug. 10, 2018 in corresponding/ related European Application No. 05004853.7.
"Prestige Cervical Disc System Surgical Technique", 12 pgs.
Adams et al., "Orientation Aid for Head and Neck Surgeons," Innov. Tech. Biol. Med., vol. 13, No. 4, 1992, pp. 409-424.
Adams et al., Computer-Assisted Surgery, IEEE Computer Graphics & Applications, pp. 43-51, (May 1990).
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 6, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensional Computer Reconstructions of Brain Lesions from Surface Contours Provided by Computed Tomography: A Prospectus," Neurosurgery, vol. 11, No. 1, Part 1, 1982, pp. 73-84.
Benzel et al., "Magnetic Source Imaging: a Review of the Magnes System of Biomagnetic Technologies Incorporated," Neurosurgery, vol. 33, No. 2, (Aug. 1993), pp. 252-259.
Bergstrom et al. Stereotaxic Computed Tomography, Am. J. Roentgenol, vol. 127 pp. 167-170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Brown, R., M.D., A Stereotactic Head Frame for Use with CT Body Scanners, Investigative Radiology .Copyrgt. J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).

(56) References Cited

OTHER PUBLICATIONS

Bucholz, R.D., et al., Intraoperative Ultrasoic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery,Grenoble, France, pp. 459-466 (Mar. 19-22, 1997).
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnel sans Contact," Quelques Applications Medicales, Jul. 1991.
Cinquin et al., "ComputerAssisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Communication pursuant to Article 94(3) EPC dated Oct. 10, 2016 for European Application No. 050048537-1666 which claims benefit of U.S. Appl. No. 10/794,716, filed Mar. 5, 22004.
Cutting M.D. et al., Optical Tracking of Bone Fragments During Craniofacial Surgery, Second Annual International Symposium on Medical Robotics and Computer Assisted Surgery, pp. 221-225, (Nov. 1995).
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, (May 1, 1994) pp. 137-145.
Germano, "Instrumentation, Technique and Technology", Neurosurgery, vol. 37, No. 2, Aug. 1995, pp. 348-350.
Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image processing, Second Edition, 1987, pp. 52-54.
Gottesfeld Brown et al., "Registration of Planar Film Radiographs with Computer Tomography," Proceedings of MMBIA, Jun. '96, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13 (1994) pp. 193-211.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Computer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.
Hatch, et al., "Reference-Display System for the Integration of CT Scanning and the Operating Microscope", Proceedings of the Eleventh Annual Northeast Bioengineering Conference, Mar. 14-15, 1985, pp. 252-524.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Lombardi, et al., "An in vivo determination of total hip arthroplasty pistoning during activity", The Journal of Arthroplasty vol. 15 No. 6 2000, pp. 702-709 (Year: 2000).

* cited by examiner

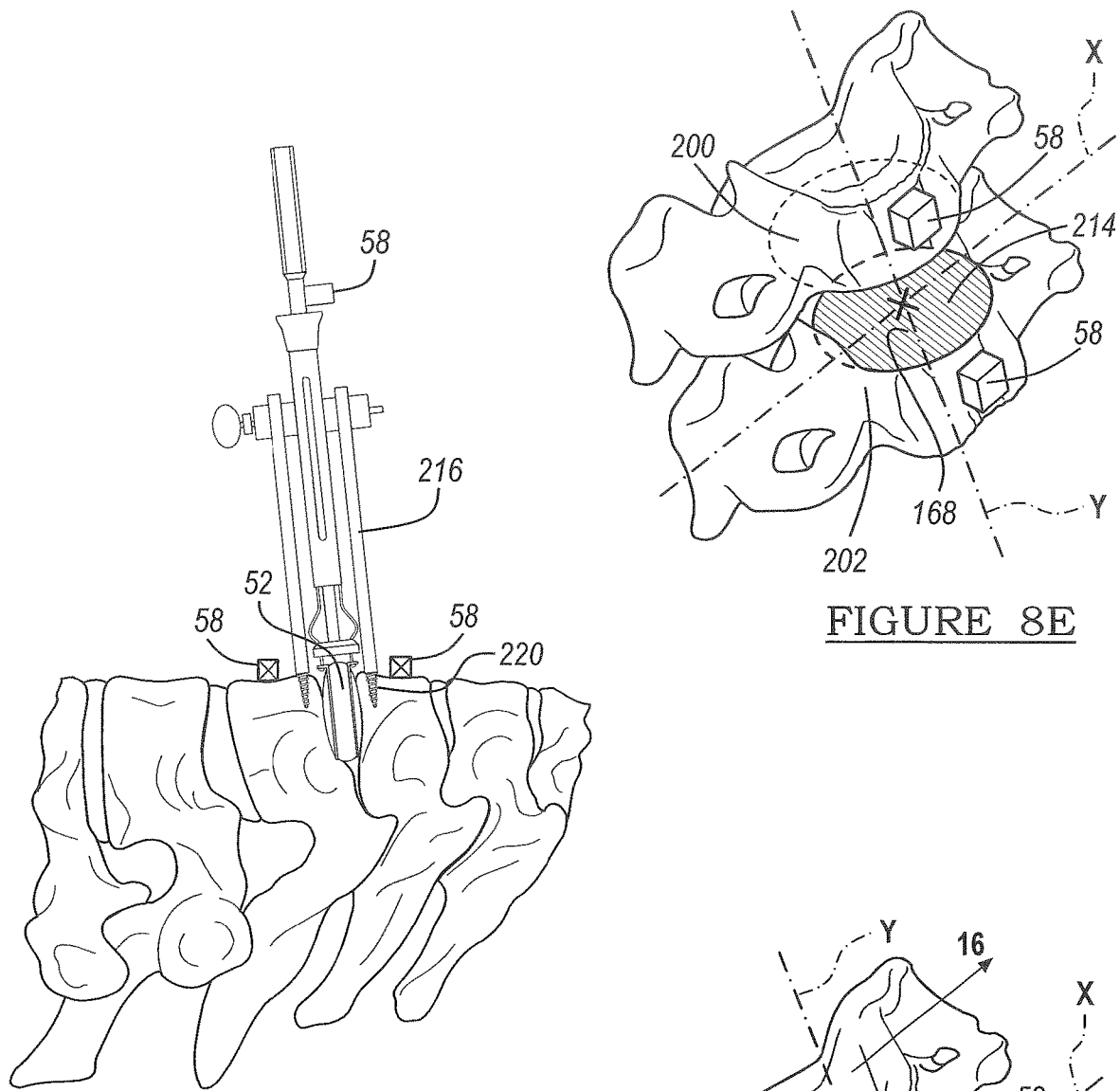
FIGURE 8E
FIGURE 8F
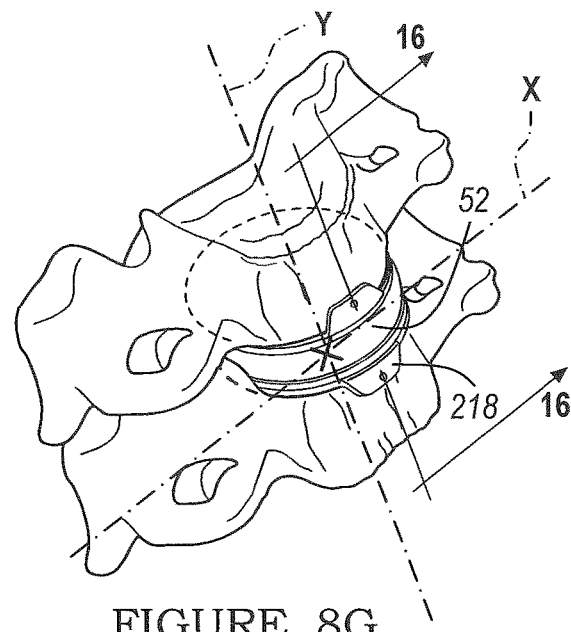
FIGURE 8G

METHOD AND APPARATUS FOR POST-OPERATIVE TUNING OF A SPINAL IMPLANT

CROSS-REFERENCE TO RELATED APPLICATIONS

This application is a divisional of U.S. patent application Ser. No. 15/868,639 filed on Jan. 11, 2018, which is a divisional of U.S. patent application Ser. No. 10/423,515 filed on Apr. 25, 2003, now U.S. Pat. No. 9,867,721 issued on Jan. 16, 2018, which is a continuation-in-part of U.S. patent application Ser. No. 10/354,562 filed on Jan. 30, 2003, now U.S. Pat. No. 7,660,623 issued on Feb. 9, 2010. The disclosures of the above applications are incorporated herein by reference.

FIELD OF THE INVENTION

The present invention generally relates to adjusting or tuning an implant, and more specifically, to pre-operative planning to select an implant and technique and post-operative tuning of the implant by a telemetric or a minimally invasive procedure.

BACKGROUND OF THE INVENTION

Image guided medical and surgical procedures utilize patient images obtained prior to or during a medical procedure to guide a physician performing the procedure. Recent advances in imaging technology, especially in imaging technologies that produce highly-detailed, computer-generated two, three and four-dimensional images, such as computed tomography (CT), magnetic resonance imaging (MRI), isocentric C-arm fluoroscopic imaging, fluoroscopes or ultrasounds have increased the interest in image guided medical procedures. During these image guided medical procedures, the area of interest of the patient that has been imaged is displayed on a display. Surgical instruments and/or implants that are used during this medical procedure are tracked and superimposed onto this display to show the location of the surgical instrument relative to the area of interest in the body.

Other types of navigation systems operate as an imageless system, where an image of the body is not captured by an imaging device prior to the medical procedure. With this type of procedure, the system may use a probe to contact certain landmarks in the body, such as landmarks on bone, where the system generates either a two-dimensional or three-dimensional model of the area of interest based upon these contacts. This way, when the surgical instrument or other object is tracked relative to this area, they can be superimposed on this model.

Most types of orthopedic medical procedures are performed using conventional surgical techniques. These techniques generally involve opening the patient in a relatively invasive manner to provide adequate viewing by the surgeon during the medical procedure. These types of procedures, however, generally extend the recovery period for the patient due to the extent of soft tissue and muscular incisions resulting from the medical procedure. Use of image guided technology in orthopedic medical procedures would enable a more minimally invasive type of procedure to be performed to thereby reduce the overall recovery time and cost of the procedure. Use of the image guided procedure may also enable more precise and accurate placement of an implant within the patient.

Once the implant has been surgically positioned within the patient, the patient's surrounding anatomy generally heals over time with the surrounding skeletal and muscular structure regaining a healthy state. However, since the implant is generally implanted when the patient is dysfunctional, this muscular and skeletal adjustment or healing may effect the subsequent range of motion, effectiveness, life expectancy of the implant, performance of the implant, and potentially cause deterioration of surround discs or implants. For example, in a spinal implant, upon the abdominal and back muscles strengthening after the implant procedure, the spine may subsequently align. This alignment may result in the implant or articulation faces of the implant being impinged because of the resultant alignment. This may result in a revision-type surgery that requires the implant to be removed and a subsequent implant being repositioned at the implant site.

The surgical procedures performed during orthopedic medical procedures, including spinal procedures, require the use of various instruments, assemblies and jigs to perform the procedure. Typically, jigs are used to support a single instrument that must be attached to the area of interest when the instrument is being used. Multiple jigs are thus typically required to be attached and removed from the area of interest as the procedure progresses. Use of multiple jigs and instruments, along with attaching and reattaching to the area of interest provides for a tedious and time consuming procedure. Moreover, inherent inaccuracies due to this procedure may provide less than acceptable results.

It is, therefore, desirable to provide a method and apparatus for post-operative adjustment or tuning of an implant, such as a spinal implant using telemetric or minimally invasive techniques. It is also desirable to provide an instrument assembly that may be attached to the implant site, such as a spinal implant site, once during the entire procedure, thereby reducing surgical time, costs, as well as increasing surgical accuracy. It is, therefore, an object of the present invention to provide such methods and apparatus for use in medical procedures.

SUMMARY OF THE INVENTION

In accordance with the teachings of the present invention, a tunable implant, system, method and associated instruments for use in implanting and adjusting the tunable implant after the implant has been positioned within the patient is disclosed. The tunable implant may be any type of implant, such as a spinal implant.

In one embodiment, a method for tuning an implant positioned within a patient is provided. This method includes analyzing the operation of the implant that is positioned within the patient, determining if any adjustment of the implant is necessary, and adjusting the implant with the implant positioned within the patient to improve implant performance.

In another embodiment, a tunable implant is positioned within the patient. The tunable implant includes a securing mechanism that is used to secure the implant within the patient. An actuation portion is used to permit the tunable implant to move. An adjustment portion is used to permit adjustment of the tunable implant after the tunable implant is positioned within the patient.

In yet another embodiment, a tunable implant system for use in adjusting a tunable implant of a patient is provided. This tunable implant system includes a tunable implant having an adjustable portion that is operable to permit adjustment of the tunable implant after the implant is positioned within the patient. A telemetric system is provided and operable to telemetrically receive data from the tunable implant where the data is used to determine adjustment of the tunable implant.

Still another embodiment, an instrument assembly for use in performing spinal surgery is provided. This instrument includes a mounting platform operable to be positioned adjacent to vertebrae. The instrument assembly also includes a jig that is operable to be removably attached to the mounting platform. The jig is also operable to support an instrument used during the spinal surgery.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 8a-8g illustrate another medical procedure employing the display according to the teachings of the present invention;

DETAILED DESCRIPTION OF THE PREFERRED EMBODIMENTS

The following description of the embodiment(s) is merely exemplary in nature and is in no way intended to limit the invention, its application, or uses. Moreover, while the invention is discussed in detail below in regard to orthopedic/spinal surgical procedures, the present invention may be used with any type of medical procedure, including orthopedic, cardiovascular, neurovascular, soft tissue procedures, or any other medical procedures.

Figure 1:
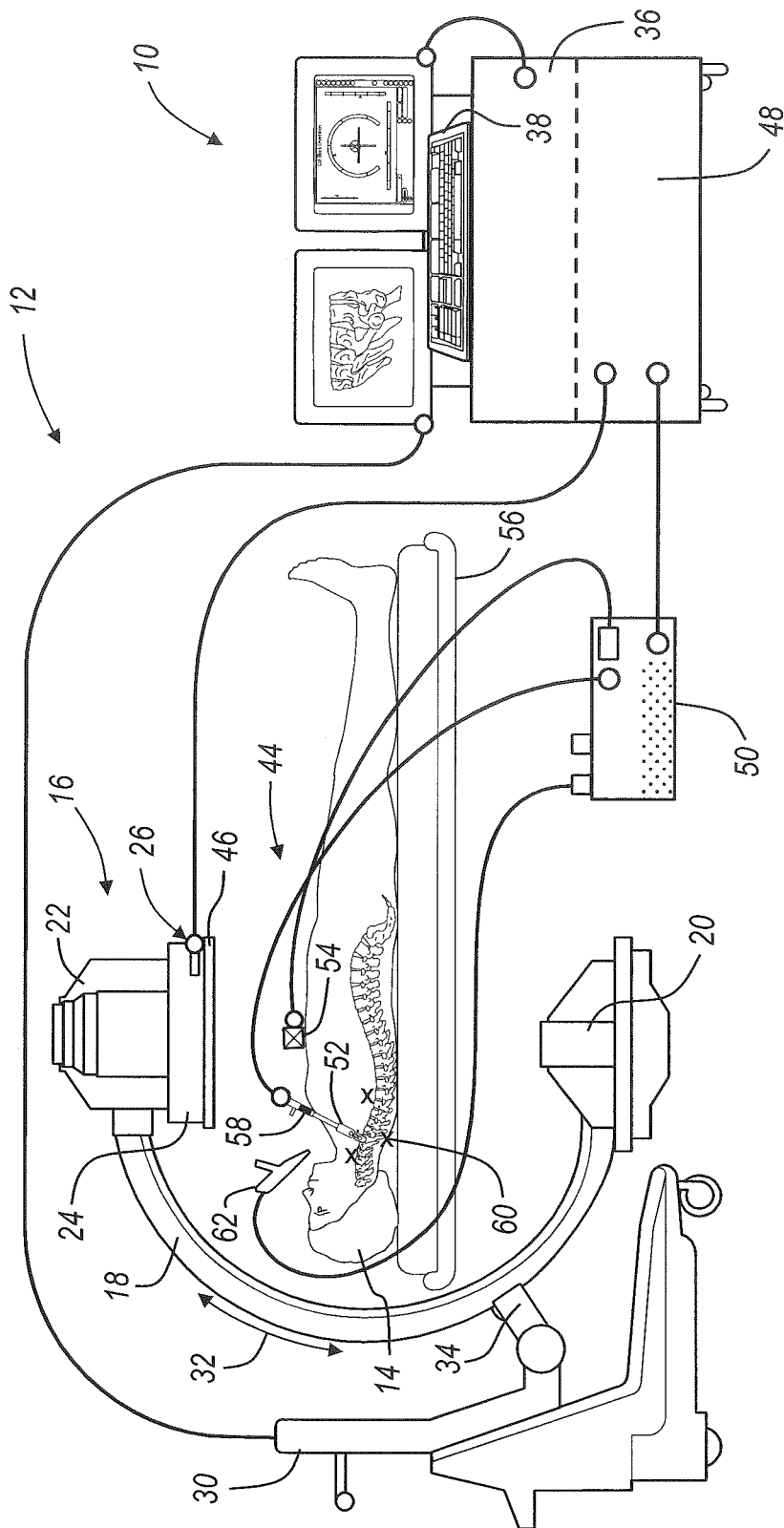
FIG. 1 is a diagram of a navigation system employing a display according to the teachings of the present invention.

FIG. 1 is a diagram illustrating a five or six degree of freedom (5 or 6 DOF) alignment display 10 employed with an image guided navigation system 12 for use in navigating a surgical instrument or implant during a medical procedure. It should also be noted that the display 10 may be used or employed in an image-less based navigation system, further discussed herein. The navigation system 12 may be used to navigate any type of instrument or delivery system, such as a reamer, impactor, cutting block, saw blade, catheter, guide wires, needles, drug delivery systems, and cell delivery systems. The navigation system 12 may also be used to navigate any type of implant including orthopedic implants, spinal implants, cardiovascular implants, neurovascular implants, soft tissue implants, or any other devices implanted in a patient 14. The navigation system 12 may also be used to navigate implants or devices that are formed as an assembly or from multiple components where the location and orientation of each component is dependent upon one another to be effective in its use. For example, during a spinal procedure, the display may be used to track and align a spinal screw with a spinal rod to insure attachment of each device.

The navigation system 12 includes an imaging device 16 that is used to acquire pre-operative or real-time images of the patient 14. The imaging device 16 is a fluoroscopic C-arm x-ray imaging device that includes a C-arm 18, an x-ray source 20, an x-ray receiving section 22, an optional calibration and tracking target 24 and optional radiation sensors 26. The optional calibration and tracking target 24 includes calibration markers 28 (see FIGS. 2a-2b), further discussed herein. A C-arm controller 30 captures the x-ray images received at the receiving section 22 and stores the images for later use. The C-arm controller 30 may also control the rotation of the C-arm 18. For example, the C-arm 18 may move in the direction of arrow 32 or rotate about the long axis of the patient 14, allowing anterior or lateral views of the patient 14 to be imaged. Each of these movements involve rotation about a mechanical axis 34 of the C-arm 18. In this example, the long axis of the patient 14 is substantially in line with the mechanical axis 34 of the C-arm 18. This enables the C-arm 18 to be rotated relative to the patient 14, allowing images of the patient 14 to be taken from multiple directions or about multiple planes. An example of a fluoroscopic C-arm x-ray imaging device 16 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, etc.

In operation, the imaging device 16 generates x-rays from the x-ray source 20 that propagate through the patient 14 and calibration and/or tracking target 24, into the x-ray receiving section 22. The receiving section 22 generates an image representing the intensities of the received x-rays. Typically, the receiving section 22 includes an image intensifier that first converts the x-rays to visible light and a charge coupled device (CCD) video camera that converts the visible light into digital images. Receiving section 22 may also be a digital device that converts x-rays directly to digital images, thus potentially avoiding distortion introduced by first converting to visible light. With this type of digital C-arm, which is generally a flat panel device, the calibration and/or tracking target 24 and the calibration process discussed below may be eliminated. Also, the calibration process may be eliminated for different types of medical procedures. Alternatively, the imaging device 16 may only take a single image with the calibration and tracking target 24 in place. Thereafter, the calibration and tracking target 24 may be removed from the line-of-sight of the imaging device 16.

Two dimensional fluoroscopic images taken by the imaging device 16 are captured and stored in the C-arm controller 30. These images are forwarded from the C-arm controller 30 to a controller or work station 36 having the display 10 that may either include a single display 10 or a dual display 10 and a user interface 38. The work station 36 provides facilities for displaying on the display 10, saving, digitally manipulating, or printing a hard copy of the received images, as well as the five or six degree of freedom display. The user interface 38, which may be a keyboard, joy stick, mouse, touch pen, touch screen or other suitable device allows a physician or user to provide inputs to control the imaging device 16, via the C-arm controller 30, or adjust the display settings, such as safe zones of the display 10, further discussed herein. The work station 36 may also direct the C-arm controller 30 to adjust the rotational axis 34 of the C-arm 18 to obtain various two-dimensional images along different planes in order to generate representative two-dimensional and three-dimensional images. When the x-ray source 20 generates the x-rays that propagate to the x-ray receiving section 22, the radiation sensors 26 sense the presence of radiation, which is forwarded to the C-arm controller 30, to identify whether or not the imaging device 16 is actively imaging. This information is also transmitted to a coil array controller 48, further discussed herein. Alternatively, a person or physician may manually indicate when the imaging device 16 is actively imaging or this function can be built into the x-ray source 20, x-ray receiving section 22, or the control computer 30.

Figure 2B:
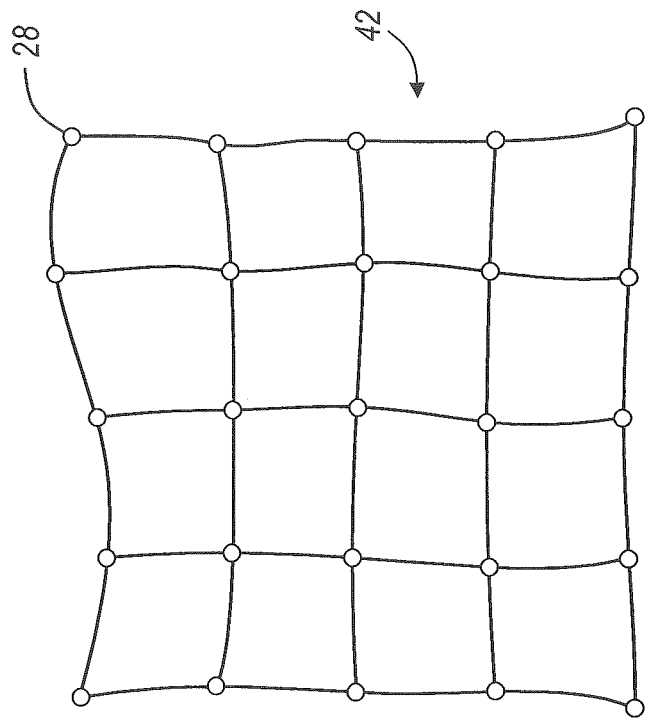
FIGS. 2a and 2b are diagrams representing undistorted and distorted views of a fluoroscopic C-arm imaging device.
Figure 2A:
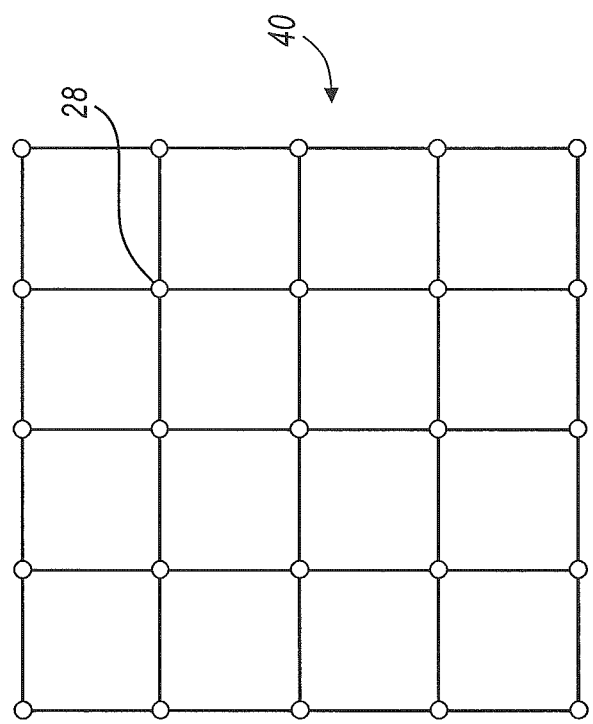

Fluoroscopic C-arm imaging devices 16 that do not include a digital receiving section 22 generally require the calibration and/or tracking target 24. This is because the raw images generated by the receiving section 22 tend to suffer from undesirable distortion caused by a number of factors, including inherent image distortion in the image intensifier and external electromagnetic fields. An empty undistorted or ideal image and an empty distorted image are shown in FIGS. 2a and 2b, respectively. The checkerboard shape, shown in FIG. 2a, represents the ideal image 40 of the checkerboard arranged calibration markers 28. The image taken by the receiving section 22, however, can suffer from distortion, as illustrated by the distorted calibration marker image 42, shown in FIG. 2b.

Intrinsic calibration, which is the process of correcting image distortion in a received image and establishing the projective transformation for that image, involves placing the calibration markers 28 in the path of the x-ray, where the calibration markers 28 are opaque or semi-opaque to the x-rays. The calibration markers 28 are rigidly arranged in pre-determined patterns in one or more planes in the path of the x-rays and are visible in the recorded images. Because the true relative position of the calibration markers 28 in the recorded images are known, the C-arm controller 30 or the work station or computer 36 is able to calculate an amount of distortion at each pixel in the image (where a pixel is a single point in the image). Accordingly, the computer or work station 36 can digitally compensate for the distortion in the image and generate a distortion-free or at least a distortion improved image 40 (see FIG. 2a). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the fluoroscopic C-arm imaging device 16 is shown in FIG. 1, any other alternative imaging modality may also be used or an image-less based application may also be employed, as further discussed herein. For example, isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), 2D, 3D or 4D ultrasound, intraoperative CT, MRI, or O-arms having single or multi flat panels receivers that move about the ring to acquire fluoroscopic images may also be used to acquire pre-operative or real-time images or image data of the patient 14. Image datasets from hybrid modalities, such as positron emission tomography (PET) combined with CT, or single photon emission computer tomography (SPECT) combined with CT, could also provide functional image data superimposed onto anatomical data to be used to confidently reach target sights within the areas of interest. It should further be noted that the fluoroscopic C-arm imaging device 16, as shown in FIG. 1, provides a virtual bi-plane image using a single-head C-arm fluoroscope 16 by simply rotating the C-arm 18 about at least two planes, which could be orthogonal planes to generate two-dimensional images that can be converted to three-dimensional volumetric images that can be displayed on the six degree of freedom display 10.

The navigation system 12 further includes an electromagnetic navigation or tracking system 44 that includes a transmitter coil array 46, the coil array controller 48, a navigation probe interface 50, an instrument 52 having an electromagnetic tracker and a dynamic reference frame 54. It should further be noted that the entire tracking system 44 or parts of the tracking system 44 may be incorporated into the imaging device 16, including the work station 36 and radiation sensors 26. Incorporating the tracking system 44 will provide an integrated imaging and tracking system. Any combination of these components may also be incorporated into the imaging system 16, which again can include a fluoroscopic C-arm imaging device or any other appropriate imaging device. Obviously, if an image-less procedure is performed, the navigation and tracking system 44 will be a stand alone unit.

The transmitter coil array 46 is shown attached to the receiving section 22 of the C-arm 18. However, it should be noted that the transmitter coil array 46 may also be positioned at any other location as well, particularly if the imaging device 16 is not employed. For example, the transmitter coil array 46 may be positioned at the x-ray source 20, within the OR table 56 positioned below the patient 14, on siderails associated with the OR table 56, or positioned on the patient 14 in proximity to the region being navigated, such as by the patient's pelvic area. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induces currents in sensors 58 positioned in the instrument 52, further discussed herein. These induced signals from the instrument 52 are delivered to the navigation probe interface 50 and subsequently forwarded to the coil array controller 48. The navigation probe interface 50 provides all the necessary electrical isolation for the navigation system 12. The navigation probe interface 50 also includes amplifiers, filters and buffers required to directly interface with the sensors 58 in instrument 52. Alternatively, the instrument 52 may employ a wireless communications channel as opposed to being coupled directly to the navigation probe interface 50.

The instrument 52 is equipped with at least one, and may include multiple localization sensors 58. In this regard, the instrument 52 may include an orthogonal pair coil sensor 58 or a tri-axial coil sensor 58 or multiple single coil sensors 58 positioned about the instrument 52. Here again, the instrument 52 may be any type of medical instrument or implant. For example, the instrument may be a catheter that can be used to deploy a medical lead, be used for tissue ablation, or be used to deliver a pharmaceutical agent. The instrument 52 may also be an orthopedic instrument, used for an orthopedic procedure, such as reamers, impactors, cutting blocks, saw blades, drills, etc. The instrument 52 may also be any type of neurovascular instrument, cardiovascular instrument, soft tissue instrument, etc. Finally, the instrument 52 may be an implant that is tracked, as well as any other type of device positioned and located within the patient 14. These implants can include orthopedic implants, neurovascular implants, cardiovascular implants, soft tissue implants, or any other devices that are implanted into the patient 14. Particularly, implants that are formed from multiple components where the location and orientation of each component is dependent upon the location and orientation of the other component, such that each of these components can be tracked or navigated by the navigation and tracking system 44 to be displayed on the six degree of freedom display 10.

In an alternate embodiment, the electromagnetic sources or generators may be located within the instrument 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization or tracking may also be used with other types of navigation systems, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. These types of localization systems include conductive, active optical, passive optical, ultrasound, sonic, electromagnetic, etc. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54 is a small magnetic field detector or any other type of detector/transmitter that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as the patient's spinal region, as shown in FIG. 1 or on any other region of the patient. The dynamic reference frame 54 can be affixed to the patient's skin, by way of a stick-on adhesive patch. The dynamic reference frame 54 may also be removably attachable to fiducial markers 60 also positioned on the patient's body and further discussed herein.

Alternatively, the dynamic reference frame 54 may be internally attached, for example, to the spine or vertebrae of the patient using bone screws that are attached directly to the bone. This provides increased accuracy since this will track any motion of the bone. Moreover, multiple dynamic reference frames 54 may also be employed to track the position of two bones relative to a joint. For example, one dynamic reference frame 54 may be attached to a first vertebra, while a second dynamic reference frame 54 may be attached to a second vertebra. In this way, motion of the spine or vertebrae may be detected by the dual dynamic reference frames 54. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference.

Briefly, the navigation system 12 operates as follows. The navigation system 12 creates a translation map between all points in the radiological image generated from the imaging device 16 and the corresponding points in the patient's anatomy in patient space. After this map is established, whenever a tracked instrument 52 is used, the work station 36 in combination with the coil array controller 48 and the C-arm controller 30 uses the translation map to identify the corresponding point on the pre-acquired image, which is displayed on display 10. This identification is known as navigation or localization. An icon representing the localized point or instrument is shown on the display 10, along with five or six degrees of freedom indicia.

To enable navigation, the navigation system 12 will detect both the position of the patient's anatomy 14 and the position of the surgical instrument 52. Knowing the location of these two items allows the navigation system 12 to compute and display the position of the instrument 52 in relation to the patient 14. The tracking system 44 is employed to track the instrument 52 and the anatomy simultaneously. While the display 10 is configured to show the instrument with six degree of freedom accuracy.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the instrument 52 by measuring the field strength at the sensor 58 location. The dynamic reference frame 54 is fixed to the patient 14 to identify the location of the patient 14 in the navigation field. The electromagnetic tracking system 44 continuously recomputes the relative position of the dynamic reference frame 54 and the instrument 52 during localization and relates this spatial information to patient registration data to enable image guidance of the instrument 52 within the patient 14.

Patient registration is the process of determining how to correlate the position of the instrument 52 on the patient 14 to the position on the diagnostic, pre-acquired, or real-time images. To register the patient 14, the physician or user will select and store particular points from the pre-acquired images and then touch the corresponding points on the patient's anatomy with a pointer probe 62. The navigation system 12 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14. The landmarks 60 can be artificial landmarks 60 that are positioned on the patient 14 or anatomical landmarks 60 that can be easily identified in the image data. The system 12 may also perform 2D to 3D registration by utilizing the acquired 2D images to register 3D volume images by use of contour algorithms, point algorithms, normalized mutual information, pattern intensity, or density comparison algorithms, as is known in the art.

In order to maintain registration accuracy, the navigation system 12 continuously tracks the position of the patient 14 during registration and navigation. This is necessary because the patient 14, dynamic reference frame 54, and transmitter coil array 46 may all move during the procedure, even when this movement is not desired. Therefore, if the navigation system 12 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

It should also be understood that localization and registration data may be specific to multiple targets. For example, should a spinal procedure be conducted, each vertebra may be independently tracked and the corresponding image registered to each vertebra. In other words, each vertebra would have its own translation map between all points in the radiological image and the corresponding points in the patient's anatomy in patient space in order to provide a coordinate system for each vertebra being tracked. The tracking system 44 would track any motion in each vertebra by use of a tracking sensor 58 associated with each vertebra. In this way, dual displays 10 may be utilized, further discussed herein, where each display tracks a corresponding vertebra using its corresponding translation map and a surgical implant or instrument 52 may be registered to each vertebra and displayed on the display 10 further assisting an alignment of an implant relative to two articulating or movable bones. Moreover, each separate display in the dual display 10 may superimpose the other vertebra so that it is positioned adjacent to the tracked vertebra thereby adding a further level of information on the six degree of freedom display 10.

As an alternative to using the imaging system 16, in combination with the navigation and tracking system 44, the five or six degree of freedom alignment display 10 can be used in an imageless manner without the imaging system 16. In this regard, the navigation and tracking system 44 may only be employed and the probe 62 may be used to contact or engage various landmarks on the patient. These landmarks can be bony landmarks on the patient, such that upon contacting a number of landmarks for each bone, the workstation 36 can generate a three-dimensional model of the bones. This model is generated based upon the contacts and/or use of atlas maps. The workstation 36 may also generate a center axis of rotation for the joint or planes, based upon the probe contacts. Alternatively, the tracking sensor 58 may be placed on the patient's anatomy and the anatomy moved and correspondingly tracked by the tracking system 44. For example, placing a tracking sensor 58 on the femur and fixing the pelvis in place of a patient and rotating the leg while it is tracked with the tracking system 44 enables the work station 36 to generate a center of axis of the hip joint by use of kinematics and motion analysis algorithms, as is known in the art. If the pelvis is not fixed, another tracking sensor 58 may be placed on the pelvis to identify the center of axis of the hip joint. If a tracking sensor 58 is placed on the femur and a tracking sensor 58 is placed on the tibia, upon moving this portion of the anatomy, a center of axis of the knee joint may be identified. Likewise, by placing a separate tracking sensor 58 on two adjacent vertebra and articulating the spine, the center of axis of the spinal region can also be identified. In this way, a target and/or model based on the center of the particular joint may be designated and identified on the six degree of freedom display 10. Movement of the instrument or implant 52 may then be tracked in relation to this target and/or model to properly align the instrument or implant 52 relative to the target and/or model.

Figure 3A:
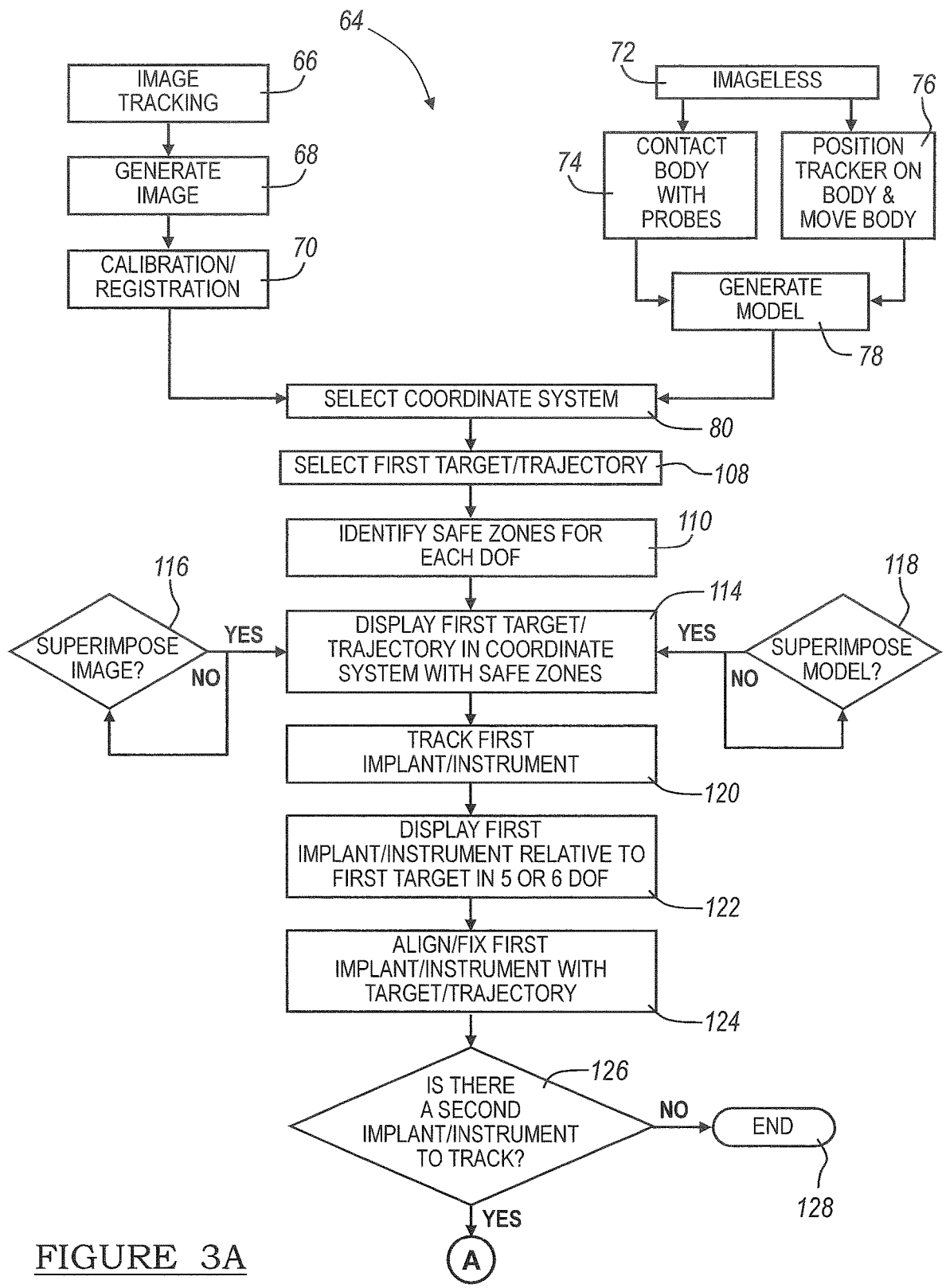
FIGS. 3a and 3b is a logic block diagram illustrating a method for employing the display according to the teachings of the present invention.
Figure 3B:
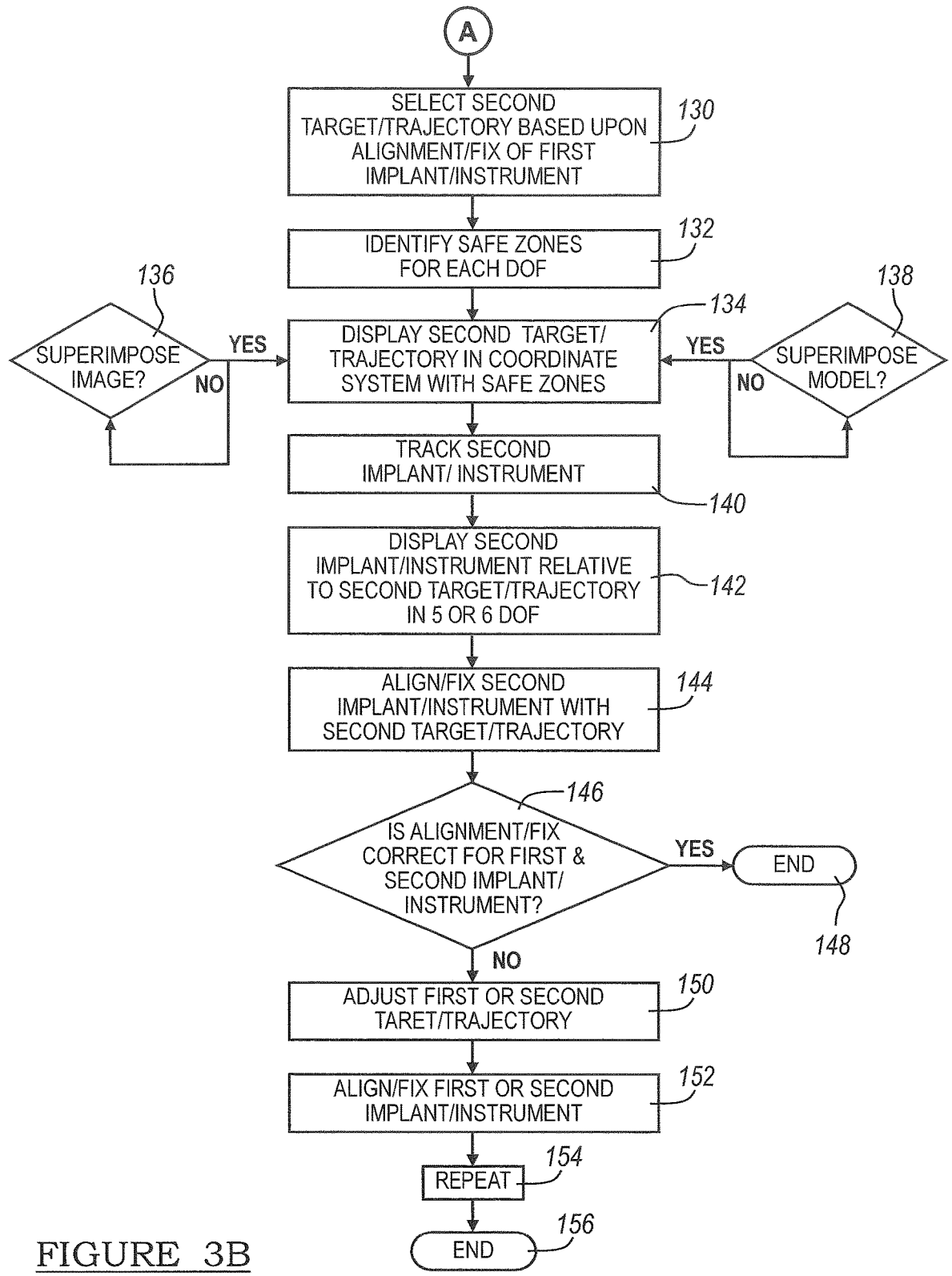

Turning to FIGS. 3a and 3b, the method of employing the six degree of freedom display 10 is described in further detail. The method 64 begins by determining whether an image based medical procedure will be employed or an image-less medical procedure will be employed. If the image based procedure is being employed, the method proceeds along the first branch. In this regard, when an image based procedure will be utilized, the method begins at block 66 identifying the image tracking procedure. From block 66, the method proceeds to block 68 where images are generated by the imaging system 16. This imaging is performed at the area of interest of the patient 14 by any type of imaging device as previously discussed. Once images have been generated at block 68, the method proceeds to block 70 where calibration and registration is performed. In block 70, calibration of the imaging device 16 takes place using the calibration targets 28. Additionally, registration of the pre-acquired images from block 68 are registered to the patient space of the medical procedure utilizing the fiducial markers 60 and probe 62 as previously discussed. This registration registers the current patient space with the pre-acquired image, so that the instrument 52 or other devices may be tracked during the medical procedure and accurately superimposed over the pre-acquired images generated from the imaging device 16.

If an image-less medical procedure is selected, the method begins at block 72 identifying that an image-less based medical procedure will be performed. This method proceeds to either block 74 identifying a first way to generate image-less models or block 76 identifying a second way to generate image-less models. At block 74, the probe 62 is used to contact the body at various anatomical landmarks in the area of interest, such as a bone. For example, by touching the probe 62 to the pelvis, knee, and ankle, articulation planes can be defined using known algorithms and the center of each joint may also be defined. An example of this type of modeling is set forth in U.S. Pat. No. 5,682,886, which is hereby incorporated by reference. Alternatively, multiple anatomical landmarks can be contacted with the probe 62 to generate a 3-D model with the more points contacted, the more accurate the model depicted.

Secondly, to generate a model at block 76, a tracking device is placed on the body and the body rotated about the joint. When this is done, the plane of rotation and joint center can be identified using known kinematic and/or motion analysis algorithms or using atlas maps or tables, as is known in the art. Once the area of interest has been probed, via block 74 or block 76, a model is generated at block 78. This model can be a 3-D surface rendered model, a 2-D model identifying articulating planes or a 3-D model identifying articulating planes and rotation, as well as the center of the joints. This enables the display 10 to use the joint centers or articulating planes as the target or trajectory, further discussed herein.

With each of the procedures 74 or 76, the procedure may be initially based on the use of atlas information or a 3-D model that is morphed, to be a patient specific model. In this regard, should the femur be the area of interest, an accurate representation of an ordinary femur may be selected from an atlas map, thereby providing an initial 2-D or 3-D model representing a typical anatomical femur. As with block 74, upon contacting numerous areas on the actual femur with the probe 62, the atlas model may be morphed into a patient specific 3-D model, with the more points contacted, the more accurate the morphed model. Patient specific information may also be acquired using an ultrasound probe to again identify the shape of the patient's natural femur in order to morph the atlas model. A fluoroscopic image of the region may also be used to morph the patient's femur with the atlas model to provide a patient specific morphed model. Proceeding under block 76 and assuming that the area of interest is the hip joint, an atlas model of the femur and pelvis may be the initial starting point. Upon rotating and moving the femur relative to the pelvis, a patient specific morphed model may be created to generate accurate joint centers and axes of motion again using known kinematics and/or motion analysis algorithms Once the image data is calibrated and registered at block 70 or the model is generated at block 78, the method proceeds to block 80. At block 80, the specific type of coordinate system is selected, which will be displayed by indicia on the six degree of freedom display 10. The coordinate systems can be a Cartesian coordinate system, a spherical coordinate system, or a polar coordinate system. By way of example, the Cartesian coordinate system will be selected. The Cartesian coordinate system will include the X, Y, and Z axes, and X rotation, Y rotation, and Z rotation about its respective axes.

Figure 5:
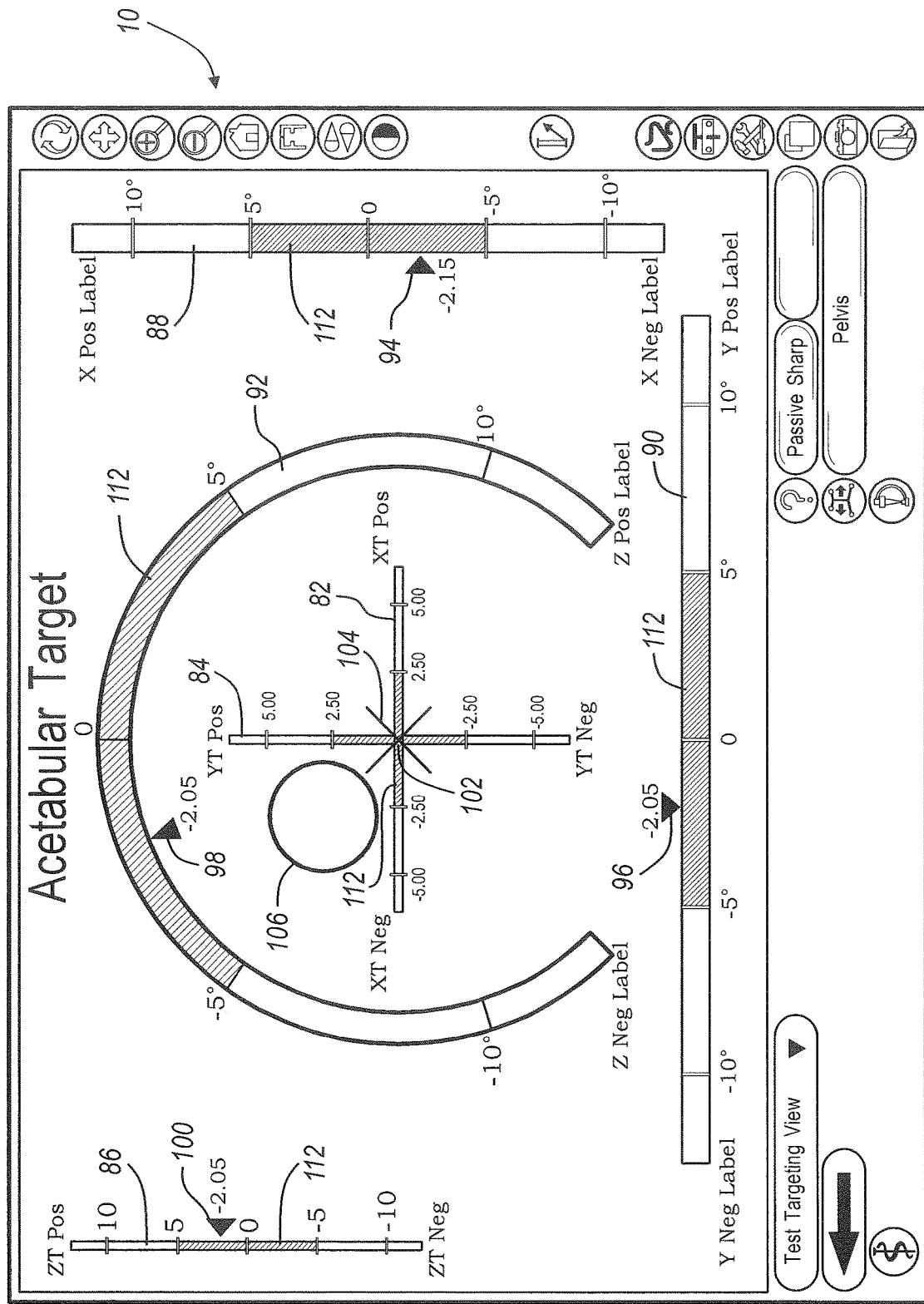
FIG. 5 is a figure of the display according to the teachings of the present invention.

With reference to FIG. 5, the six degree of freedom display 10 is shown in further detail employing the Cartesian coordinate system. In this regard, the X axis 82 and the Y axis 84 are shown positioned on the display 10. The Z axis 86 extends out from the display 10 and is shown in the upper left corner. Rotation about the X axis is shown by bar graph 88 to the right of the display 10 and rotation about the Y axis is shown by bar graph 90 positioned at the bottom of the display 10. Rotation about the Z axis is shown with the arcuate bar graph 92 oriented about the X and Y axes 82 and 84. Each axis, as well as the rotation axes identified by the bar graphs may be color coded to identify safe zones or regions for the item being tracked or navigated. In this regard, the safe zones can be defined as ranges around the planned trajectory path or target where the safe zones are determined by manufactured determined parameters, user determined parameters or patient specific parameter, further discussed herein.

Arrow indicator 94 identifies the degree of rotation about the X axis 82. Arrow indicator 96 shows the amount of rotation about the Y axis 84. Arrow 98 identifies the rotation about the Z axis, while arrow 100 identifies the depth being tracked along the Z axis 86. The origin 102 may be set to be the desired target position or trajectory path. The crosshairs 104 represents the tip of the instrument 52 being tracked, while the circle 106 represents the hind area of the instrument 52 being tracked. With the understanding that the instrument 52 can be any type of medical device or implant. Also, if five degree of freedom information is provided, one of the indicia 82, 84, 86, 88, 90, and 92 will be removed.

Once the coordinate system is selected at block 80, the method proceeds to block 108 where the target or trajectory is selected. The target or trajectory selected at block 108 is typically positioned at the origin 102 on the display 10. In this way, the object being tracked or aligned may be tracked and aligned about the origin 102. Alternatively, the target may be identified at any coordinate within the display 10 or multiple targets may also be identified within the single display 10. An indicia of the target may also be positioned on the display 10. The target is selected based upon the desired area to position the instrument 52 and can be selected from the pre-acquired images or from the 3-D model. Once selected, this target is correlated to the display 10 and generally positioned at the origin 102.

Once the target/trajectory is selected at block 108, such as the origin 102, the method proceeds to block 110 where the safe zones are identified for each degree of freedom. Referring again to FIG. 5, the safe zones 112 are identified for each degree of freedom by color coding. For example, the safe zone 112 for the X axis is between −2.5 and +2.5. The safe zone 112 for rotation about the X axis is between −50 and +5° of rotation about the X axis. The user can simply guide the instrument 52 using the cross hairs 104 and circle 106 to align the instrument 52 within these designated safe zones 112. Again, these safe zones 112 may be determined by manufacture specifications, such as tolerance range of the instruments or positions for implants. The safe zones 112 may also be determined based on the patient, the surgeon conducting the procedure, or any other factors to assist a surgeon in navigating the instrument 52 through the patient 14. These safe zones 112 may also be identified via an audible signal or tone or a varying tone. The safe zones 112 may also be identified by any other convenient manner to be set out on the display 10.

Figure 6:
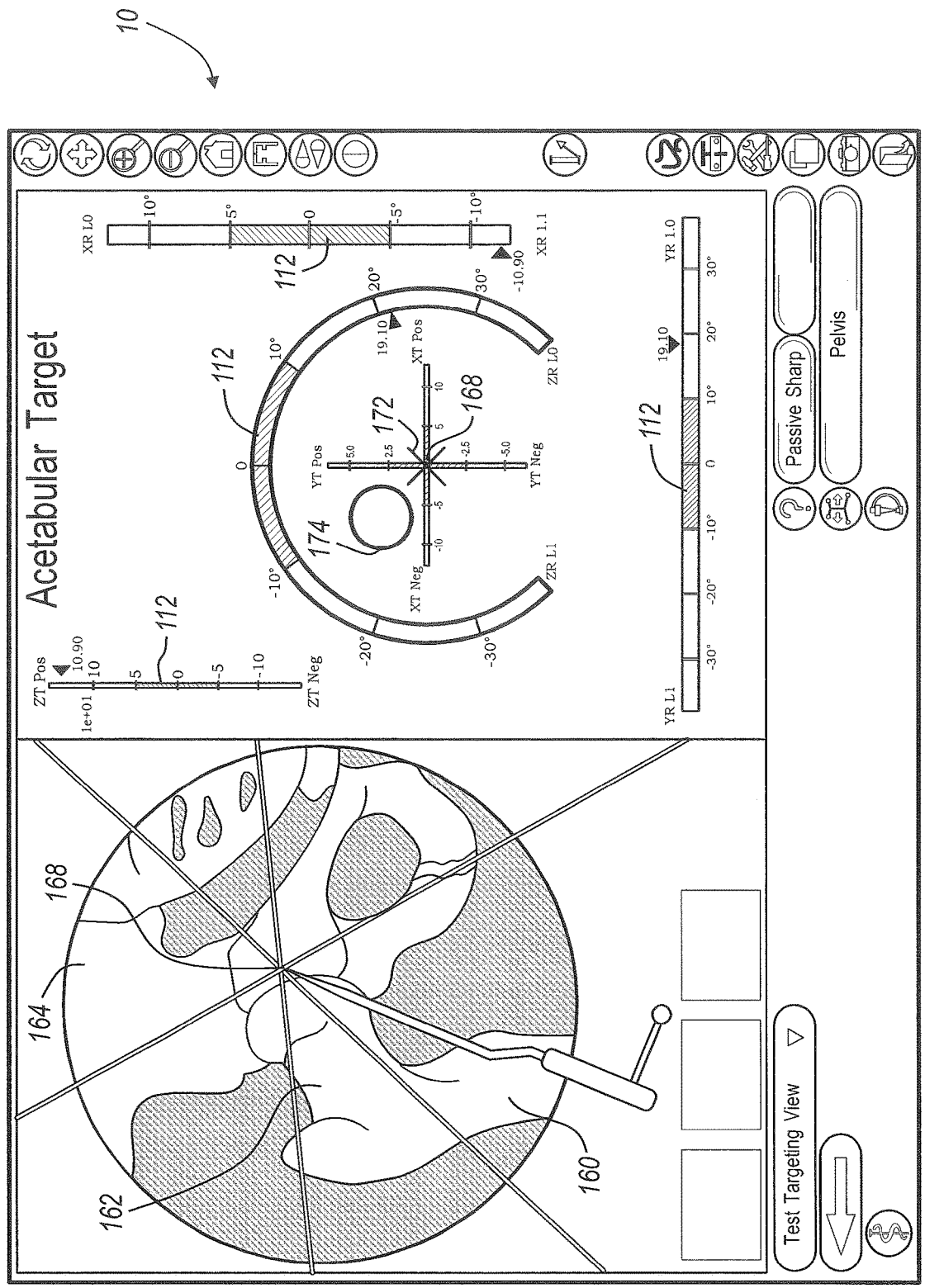
FIG. 6 is a split screen view of the display according to the teachings of the present invention.

Once the safe zones 112 are identified for each degree of freedom in block 110, the method proceeds to block 114 where the target trajectory in the selected coordinate system is displayed with the safe zones 112, as shown in FIG. 5. At block 116, if an image based method is being conducted, a decision whether to superimpose the image over the target/trajectory is made. Alternatively, the image may be placed adjacent to the target trajectory display, as is shown in FIG. 6, and further discussed herein. Should the image-less based medical procedure be conducted, at block 118, a determination is made whether to superimpose the model that was generated at block 78. Here again, this model may be superimposed over the target/trajectory display on display 10 or may be positioned adjacent to the target/trajectory display in a split screen or on a separate display.

Once the target/trajectory 102 is displayed along with the safe zones 112 in the proper coordinate system, as shown in FIG. 5, the method proceeds to block 120 where the first implant/instrument 52 is tracked with the navigation system 44. With the implant/instrument 52 being tracked at block 120, the method proceeds to block 122 wherein indicia representing the implant/instrument 52 is displayed on the display 10, with either five or six degrees of freedom information. Here again, referring to FIG. 5, the indicia representing the implant/instrument 52 is the crosshairs 104 and the circle 106 designating the tip and hind, respectively. The tip 104 and hind 106 is represented in relation to the target/trajectory path 102 in six degrees of freedom. This six degrees of freedom include the X and Y locations, as well as the depth Z of the implant/instrument 52 displayed. In addition, the rotation about each of the axes is also provided. This rotation can be helpful in many applications, including orthopedic, where rotation specific components need to be positioned relative to one another. For example, in a spinal application, alignment of a pedicle screw in relation to a spinal rod, would require information regarding the rotation of the screw relative to the rod. In cardiac procedures, this may be useful where ablation is necessary on a certain side of an artery and the ablation electrode is only positioned on one side of the catheter. In this situation, rotation of the catheter relative to the target in the artery is critical. In a neuro procedure, a biopsy needle may only have a biopsy port positioned upon one portion of the circumference of the needle, thereby requiring the rotation of the biopsy needle to be known in order to provide the proper capture of the relevant biopsy sample. Without this display, this information would not be available.

With the indicia of the implant/instrument 52 being displayed, the implant/instrument 52 is aligned or fixed with the target/trajectory 102 at block 124. In this regard, the tip 104 and the hind 106 are aligned and fixed relative to the target/trajectory 102 at the origin and the rotational orientation is also aligned to the desired position. Again, the target/trajectory 102 may not be positioned at the origin and can be positioned anywhere within the coordinate system if desired. As shown in FIG. 5, the tip 104 of the implant/instrument 52 is shown aligned with the target 102, while the hind 106 is slightly offset from the target/trajectory 102. Once the implant/instrument 52 is aligned and fixed relative to the target/trajectory 102, the method proceeds to block 126.

At block 126, a determination is made as to whether there is a second implant/instrument 52 to be tracked. If there is not a second implant/instrument 52 to be tracked, the method ends at block 128. Should there be a second implant/instrument 52 to track, such as a corresponding implant component that articulates with the first implant, the method proceeds to block 130. At block 130, a second target/trajectory 102 is selected, which is based upon the alignment or fixation of the first implant/instrument 52 relative to the first target/trajectory 102. In this regard, if the surgeon is not able to position the first implant/instrument 52 at the desired target/trajectory 102, this offset from the target/trajectory 102 may affect the second implant, which possibly articulates or mates with the first implant. If this is the case, the second target/trajectory 102 will need to take into consideration this offset in order to provide proper articulation and alignment of the first implant component with the second implant component.

With minimally invasive types of procedures, the implant may also have numerous components with each component articulating or mating with another component, thereby requiring tracking of each component as it is implanted during the minimally invasive procedure. This second target/trajectory 102 may be displayed on a separate display 10 (see FIG. 1), positioned via a split screen of a single display 10 or may be superimposed upon the existing display that displays the first target 102 and implant position. In this way, orientation and placement of both the first and second implants, which are dependent upon one another can be shown in the display 10 providing the surgeon the opportunity to adjust either position of either implant intraoperatively before the implants are permanently affixed to the patient 14. These types of implants include knee implants, hip implants, shoulder implants, spinal implants, or any other type of implant, which has a bearing surface and an articulating surface or any type of implant having multiple mating and connecting components.

Once the second target/trajectory 102 has been selected at block 130, the method proceeds to block 132. At block 132, the safe zones 112 for each degree of freedom is selected for the second implant/instrument 52 similar to the way the first set of safe zones 112 were selected for the first implant/instrument 52. Once the second safe zones 112 are selected, the method proceeds to block 134. At block 134, the display 10 displays the second target/trajectory 102 in the same coordinate system with the second safe zones 112. Here again, at block 136, if it is an image based medical procedure, the pre-acquired image may be superimposed on to the target/trajectory 102. Alternatively, this image can be positioned adjacent the target screen in a split screen configuration (see FIGS. 6 and 7). If the method is proceeding as an image-less type medical procedure, at block 138, decision is made whether to superimpose the generated model from block 78. Once the target/trajectory 102 is in the proper coordinate system with the safe zone 112 are displayed at display 10, the surgical implant/instrument 52 is tracked at block 140. Here again, the second implant/instrument 52 can be tracked on a separate display 10 or be tracked on the same display as the first implant/instrument 52.

Alternatively, separate displays 10 may be used where information is linked between the displays showing the second implant/instrument 52 in relation to the first implant/instrument 52. With the second implant/instrument 52 being tracked at block 140, the second implant/instrument 52 is displayed in relation to the second target/trajectory 102 in five or six degrees of freedom at block 142. Again, this may be a separate display 10, a split screen display 10 with both the first target/trajectory 102 and the second target/trajectory 102 or the same display 10 displaying both targets/trajectories 102. While the second implant/instrument 52 is being displayed, the second implant/instrument 52 is aligned and fixed at the second target/trajectory 102 at block 144. Once the second implant/instrument 52 is fixed at block 144, the method proceeds to block 146.

At block 146, a determination is made whether the alignment or fixation of the first and second implants/instruments 52 are correct. In this regard, with two separate displays 10 linked or with a single display 10, showing both targets/trajectories 102, a surgeon can determine whether each implant/instrument 52 is within its desired safe zones 112 and, therefore, optimally positioned for proper articulation. Here again, these safe zones 112 may be color coded for the different safe zones provided. If both implants are positioned and fixed at the proper targets, the method ends at block 148. If one or both of the implants are not properly positioned, adjustment of the first or second target/trajectory 102 is performed at block 150. Once either or both targets are adjusted, realignment of the first and/or second implants/instruments 52 are performed at block 152. Here again, since multiple component implants are dependent upon one another with respect to their position and orientation, alignment and adjustments of the targets/trajectories 102 may be performed several times until the optimum placement for each is performed at repeat block 154. Thereafter, the method terminates at end block 156.

While the above-identified procedure is discussed in relation to an orthopedic medical procedure in which an implant having multiple implant components is implanted within a patient using the six degree of freedom display 10, it should be noted that the six degree of freedom display 10 may be used to track other medical devices as well. For example, as was briefly discussed, an ablation catheter generally has an electrode positioned only on one angular portion of its circumference. Likewise, the wall of an artery typically has a larger plaque build-up on one side. Therefore, it is desirable to align that ablation electrode with the proper side of the artery wall during the procedure. With the six degree of freedom display 10, the surgeon can easily identify the location, depth and angular rotation of the catheter relative to the artery wall. Other types of procedures may require the medical instrument or probe to be properly oriented and located within the patient, such as identifying and tracking tumors, soft tissue, etc. By knowing and displaying the six degree of freedom movement of the medical device on the display 10, the medical procedure is optimized.

It should also be pointed out that the method discussed above requires that the implant/instrument 52 have a tracking sensor associated therewith in order to identify the location of the tracked device in six degrees of freedom and display it on the display 10. The tracking sensors may be attached directly to implants, attached to the instruments that engage the implants or attach to members extending out from the implants. These tracking sensors again may be electromagnetic tracking sensors, optical tracking sensors, acoustic tracking sensors, etc. Examples of various targets, which may or may not be superimposed on the display again include orthopedic targets, spinal targets, cardiovascular targets, neurovascular targets, soft tissue targets, etc. Specific examples include again the location of the plaque on a wall of an artery, the center of an articulating joint being replaced, the center of the implant placement, etc. By displaying two targets, either on separate displays or on the same display, the surgeon can dynamically plan and trial implant placements by moving one component of the implant to see where the other articulating component of the implant should be positioned. In this way, the surgeon can trial the implant confirming its placement and orientation, via the display 10 before the implant is permanently affixed to the patient 14.

In a spinal procedure, two adjacent vertebra bodies can be tracked and displayed on two separate displays. In this way, if a single jig, such as a cutting jig is used to cut both the surface of the first vertebra and the surface of the second vertebra, orientation of the jig may be displayed on each separate display in relation to the corresponding vertebra being acted upon, thereby enabling simultaneous tracking of the two planes being resected for each separate vertebra on a dual display system. Additionally, each vertebra may be displayed on each of the dual displays so that the vertebra being tracked is shown with the adjacent vertebra superimposed adjacent thereto. Once the vertebra bodies are prepared, the implant is typically placed between each vertebra on the prepared site. Other ways of preparing this site is by using drills, reamers, burrs, trephines or any other appropriate cutting or milling device.

Briefly, the method, as shown in FIGS. 3a and 3b, demonstrates that the display 10 illustrated both the position and orientation of an object with respect to a desired position and orientation with six degrees of freedom accuracy. The display 10 may be automatically updated in real-time using the navigation system 44 to report the orientation of the tracked device. The user may also adjust the display 10 in order to control a device's orientation. The display 10 again consists of three rotational indicators (RX, RY, RZ) and three translational indicators or indicia (TX, TY, TZ). Each indicator shows both visual and quantitative information about the orientation of the device. Each indicator also displays a predetermined safe zone 112 and application-specific label for each degree of freedom. As noted, it may also be relevant to overlay the display 10 over anatomical image data from the imaging device 16. When working with 3-D image data sets, the anatomy normal to the tip 104 of the positioned device can provide the user with additional positional information.

Tones, labels, colors, shading, overlaying with image data can all be modified and incorporated into the display 10. The current display 10 is also shown as a Cartesian coordinate based display, but again could be based on a polar based display or a spherical based display and a quick switch between both can be supplied or simultaneously displayed. The display can also be configured by the user to hide parameters, location, size, colors, labels, etc.

Some medical applications that may be commonly displayed and linked to the display 10 are: 1) reaming of an acetabular cup with major focus upon RY and RZ, 2) length of leg during hip and knee procedures focused upon TZ and RZ, 3) biopsies and ablations focused upon RX, RY, and RZ for direction of the therapy device, and 4) catheters with side ports for sensing information or delivery of devices, therapies, drugs, stem cells, etc. focused upon six degree of freedom information.

Figure 4B:
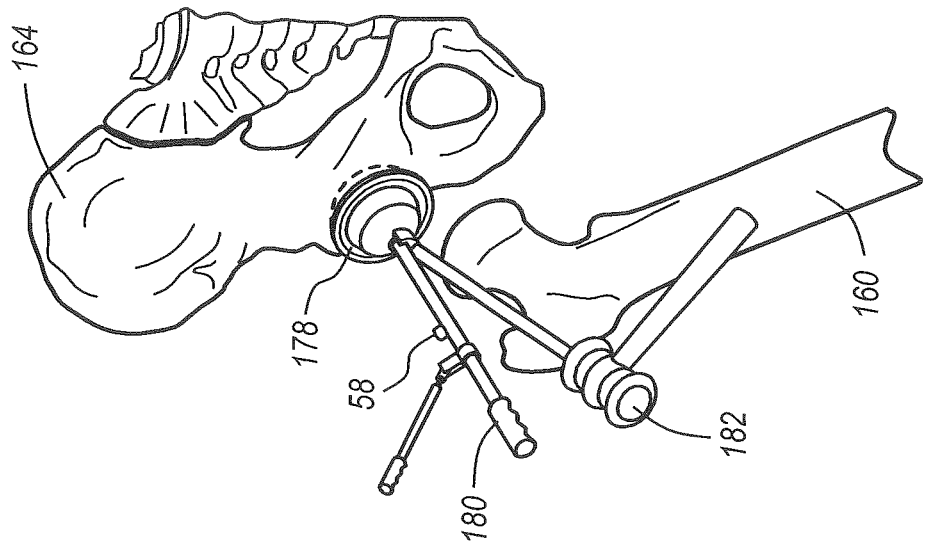
FIGS. 4a-4e illustrate a medical procedure employing the display according to the teachings of the present invention.
Figure 4A:
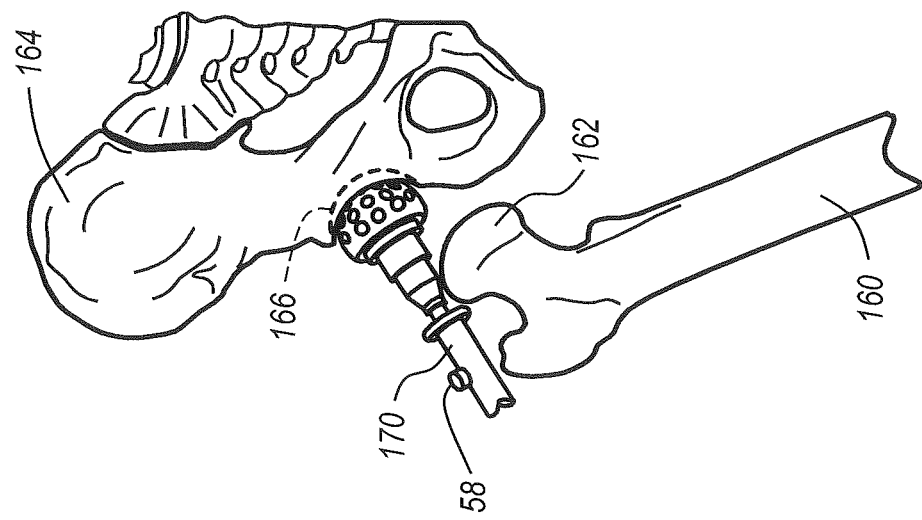
Figure 4E:
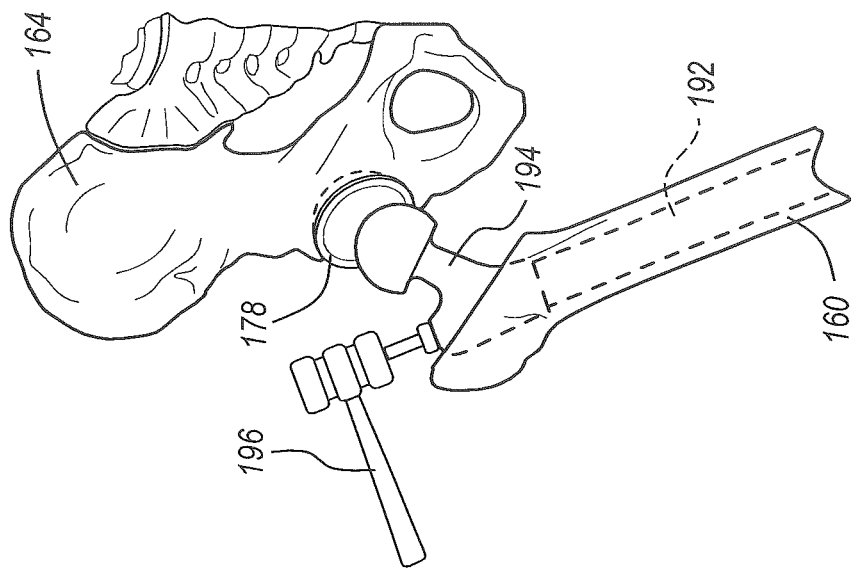

Referring now to FIGS. 4a-4e, a medical procedure employing a six degree of freedom alignment display 10 is shown in further detail. In this example, an orthopedic medical procedure replacing the hip joint is illustrated. During this procedure, various instruments 52, as well as the implants 52 are tracked and aligned using the six degree of freedom display 10. Referring specifically to FIG. 4a, a femur 160 having a femoral head 162 is illustrated, along with a pelvis 164 having an acetabulum 166. Assuming that the medical procedure being performed is an image based system, this area of interest will be imaged by the imaging device 16. Here again, the dynamic reference frame 54 may be attached to the femur 154 or the pelvis 164 or two dynamic frames 54 may be attached, one to each bone to provide additional accuracy during the medical procedure. With the head 162 dislocated from the acetabulum 166, a center of articulation of the acetabulum 166 is identified as the target 168, shown in FIG. 6.

In this regard, FIG. 6 illustrates the display 10 configured as a split screen with the right identifying the six degree of freedom display and the left illustrating the pre-acquired image with the center of articulation 168 being the intersection of the X, Y, and Z axes. As illustrated in FIG. 4a, a reamer 170 having a tracking sensor 58 is shown reaming the acetabulum 166. The tracking system 44 is able to accurately identify the navigation of the tip and hind of the reamer 170. As illustrated in FIG. 6, in the right half of the split screen, one can observe that the tip represented by the crosshairs 172 is properly positioned along the X and Y coordinates and within the corresponding safe zones 112, however, the hind portion of the instrument 170, as identified by the circle 174, is angularly offset from the target 168 at the origin. The surgeon can then angularly adjust the hind portion 174 of the instrument 170 until the hind portion 174 is shown in the display 10 as positioned over the crosshairs 172, thereby assuring proper alignment of the reaming device 170 for subsequent proper placement of the acetabular cup implant. By tracking the reamer 170, the surgeon can be relatively confident that an acetabular cup implant will be properly positioned before the implant is even impacted into the acetabulum 166.

Figure 7:
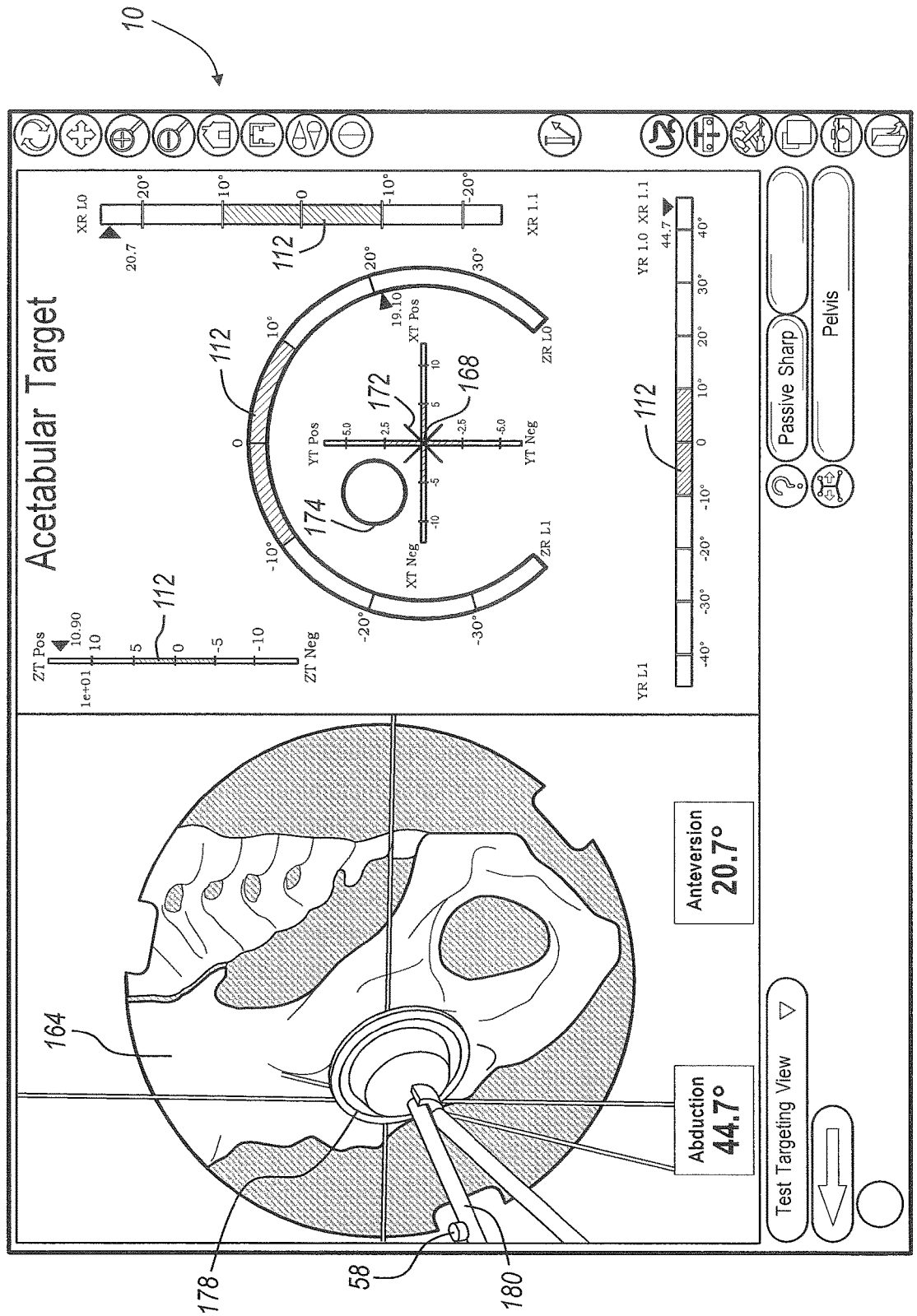
FIG. 7 is an additional split screen view of the display according to the teachings of the present invention.

Turning to FIG. 4b, an acetabular cup 178 is shown being impacted into the reamed acetabulum 166, via the tracked guide tool 180 with an impactor 182. The guide tool 180 has a distal end, which is nestingly received within the acetabular cup 178. Thus, by tracking the instrument 180, via tracking sensor 58, orientation of the acetabular cup 178 may be displayed on the display 10 in six degrees of freedom. In this way, before the acetabular cup 178 is impacted into the acetabulum 166, the surgeon can view on the display 10 whether the acetabular cup 178 is properly positioned at the proper angular orientation, as shown in FIG. 7, the impactor 180 is shown superimposed over an image generated by the imaging device 16. In this way, the proper orientation, including abduction and anteversion is achieved before the acetabular cup 178 is permanently implanted.

Once the acetabular cup 178 has been impacted, the femoral head 162 is resected along a plane 184 by use of a cutting guide 186, having the tracking sensor 58 and a saw blade 188. By using the center of the femoral head 162 as the second target, the cutting plane 184 may be properly defined to provide proper articulation with the acetabular cup 178 before a hip stem is implanted in the femur 160. Here again, the second target is dependent upon the first target. Thus, if the acetabular cup 178 was implanted somewhat offset from its target, the second target may be properly compensated to accommodate for this offset by use of the display 10. In this regard, a second display illustrating the target for the cutting plane 184 may be provided.

Figure 4D:
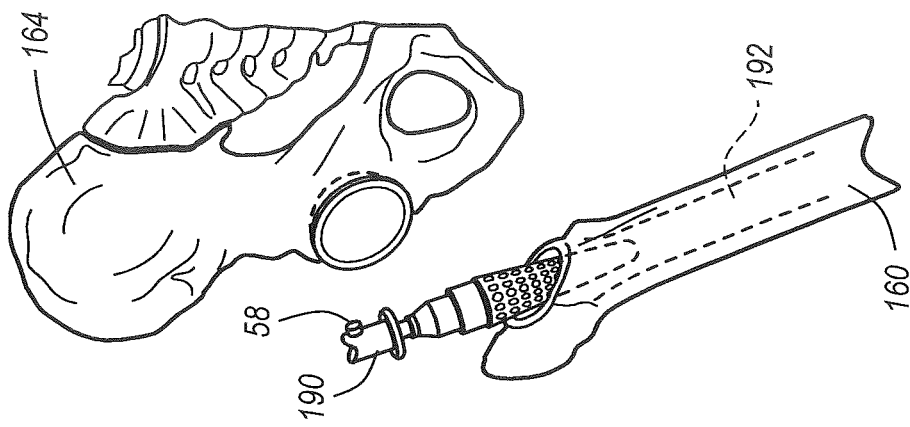
Figure 4C:
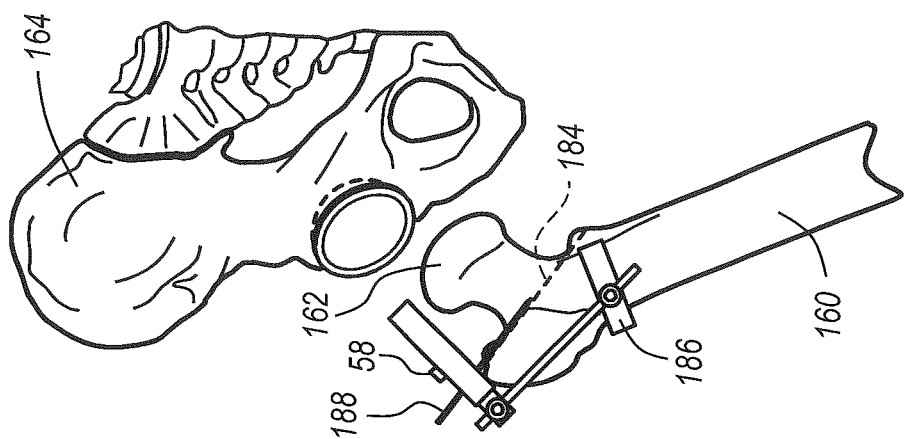

Once the femoral head 162 of the femur 160 has been resected, as shown in FIG. 4d, a reamer 190 is employed to ream out the intramedullary canal 192 of the femur 160. In order to provide proper angular orientation of the reamer 190, as well as the depth, a subsequent target can be defined and identified on the display 10 and tracked by use of the tracking sensor 58. This target may be displayed separately or in combination with the previously acquired targets. By insuring the proper angle of the reamer 190 relative to the longitudinal axis of the femur 160 is tracked and displayed on display 10, the surgeon can be provided a higher level of confidence that the hip stem will be properly positioned within the intramedullary canal 192.

Once the intramedullary canal 192 has been reamed by the reamer 190, a hip stem 194 is impacted with an impactor 196 into the intramedullary canal 192. By targeting the acetabular cup location, along with the resection plane 184 and the reaming axis of the reamer 190, upon positioning the hip stem 194, within the femur 160, proper articulation and range of motion between the acetabular cup 178 and the hip stem 194 is achieved without time consuming trialing as is conducted in conventional orthopedic procedures. Thus, by providing the safe zones 112 in relation to the hip stem 194 size, proper articulation with the acetabular cup 178 is achieved. Here again, while an example of an orthopedic hip replacement is set out, the six degree of freedom display 10 may be utilized with any type of medical procedure requiring visualization of a medical device with six degree freedom information.

The six degree of freedom display 10 enables implants, devices and therapies that have a specific orientation relative to the patient anatomy 14 to be properly positioned by use of the display 10. As was noted, it is difficult to visualize the correct placement of devices that require five or six degree of freedom alignment. Also, the orientation of multiple-segment implants, devices, or therapies in five and six degrees of freedom so that they are placed or activated in the correct orientation to one another is achieved with the display 10. Since the location and orientation is dependent upon one another to be effective, by having the proper orientation, improved life of the implants, the proper degrees of motion, and patient outcome is enhanced. Also, the six degree of freedom display 10 may be used as a user input mechanism by way of keyboard 38 for controlling each degree of freedom of a surgical robotic device. In this regard, the user can input controls with the joystick, touch screen or keyboard 38 to control a robotic device. These devices also include drill guide holders, drill holders, mechanically adjusted or line devices, such as orthopedic cutting blocks, or can be used to control and drive the alignment of the imaging system 16, or any other type of imaging system.

Since multiple implants and therapies, or multi-segment/compartment implants require multiple alignments, the display 10 may include a stereo display or two displays 10. These displays may or may not be linked, depending on the certain procedure. The target point/location (translation and orientation of each implant component is dependent upon the other implant placement or location). Therefore, the adjustment or dynamic targeting of the dependent implant needs to be input to the dependent implant and visually displayed. Again, this can be done by two separate displays or by superimposing multiple targets on a single display. Many implants such as spinal disc implants, total knee and total hip replacements repair patient anatomy 14 by replacing the anatomy (bone, etc.) and restoring the patient 14 to the original biomechanics, size and kinematics. The benefit of the six degree of freedom alignment display 10 is that original patient data, such as the images can be entered, manually or collectively, via the imaging device 16 or image-less system used for placement of the implant. Again, manually, the user can enter data, overlay templates, or collect data, via the imaging system 16. An example, as discussed herein of an application is the alignment of a femoral neck of a hip implant in the previous patient alignment. The previous patient alignment can be acquired by landmarking the patient femoral head by using biomechanics to determine the center and alignment of the current line and angle of the femoral head. This information can be used as the target on the display 10 in order to properly align the implant replacing the femoral head.

The six degree of freedom display 10 also provides orientation guidance on a single display. Separate visual and quantitative read-outs for each degree of freedom is also displayed on the display 10. Visual representations or indicia of procedure-specific accepted values (i.e., a "safe zone 112") for each degree of freedom is also clearly displayed on the display 10. These safe zones 112 are displayed as specifics or ranges for the user to align or place within. The procedure specific accepted values for the safe zones 112 can be manufacture determined, user determined, patient specific (calculated) or determined from algorithms (finite element analysis, kinematics, etc. atlas or tables). It can also be fixed or configurable. Safe zones 112 can also be defined as ranges around a planned trajectory path or the specific trajectory path itself (range zero). The trajectory paths are input as selected points by the user or paths defined from the patient image data (segmented vascular structure, calculated centers of bone/joints, anatomical path calculated by known computed methods, etc.).

Figure 8A:
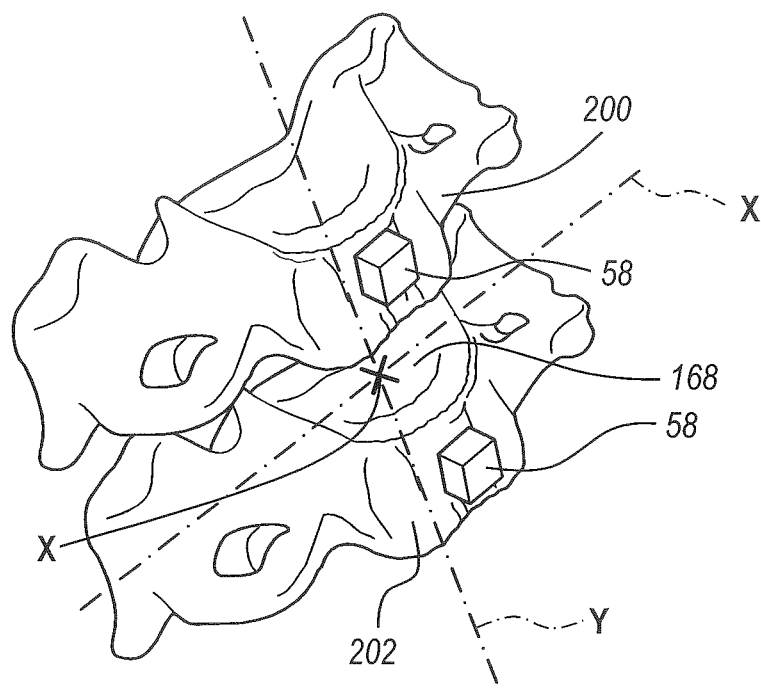
Figure 8B:
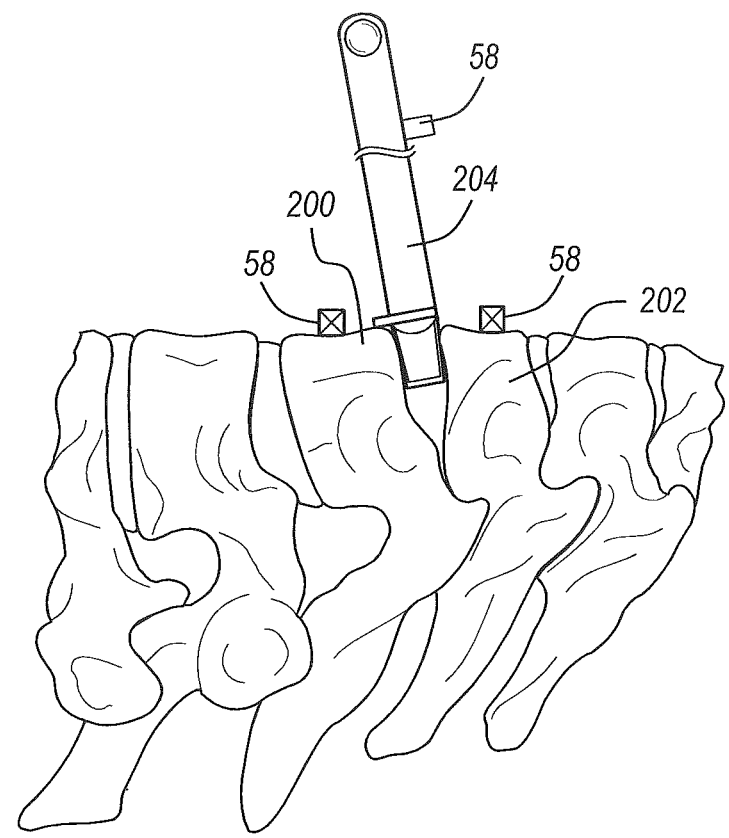
Figure 8C:
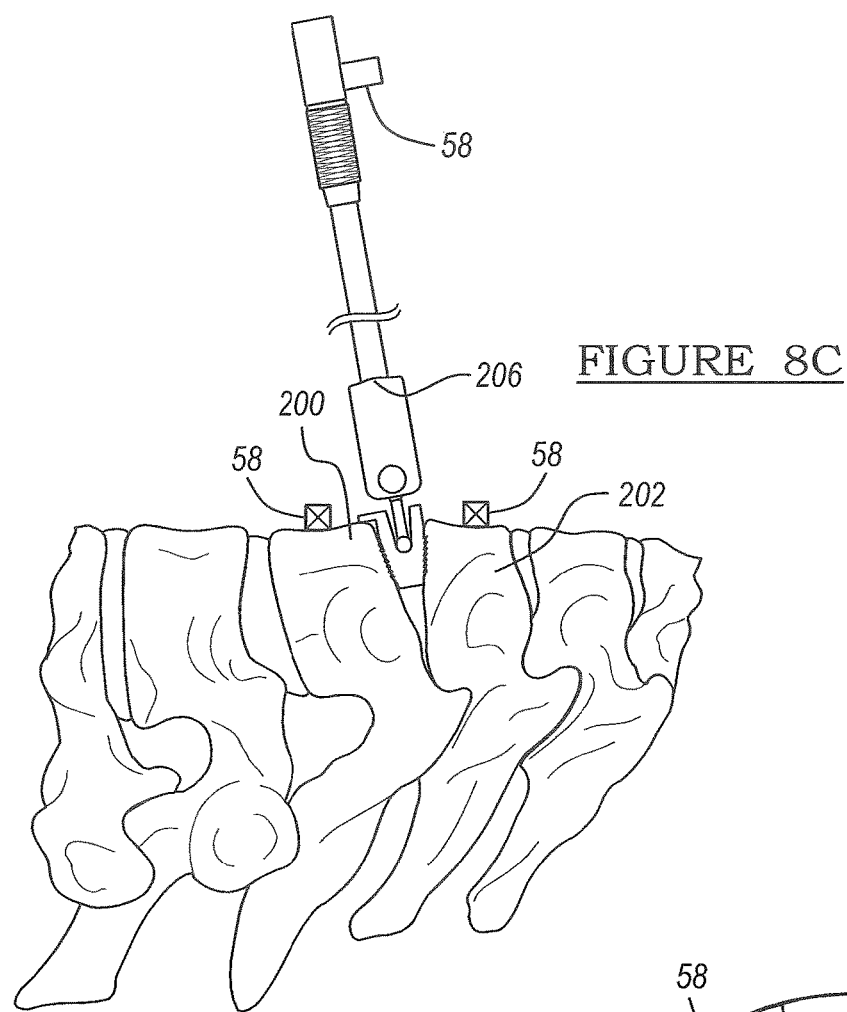
Figure 8D:
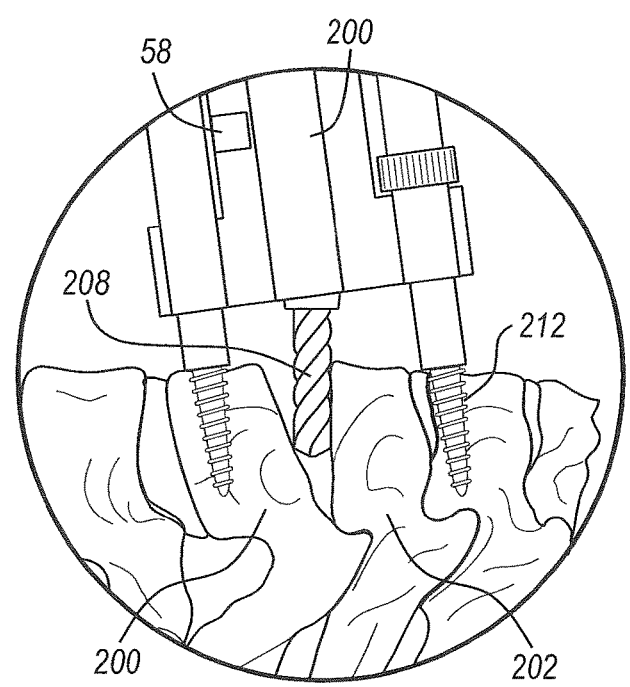
Figure 9:
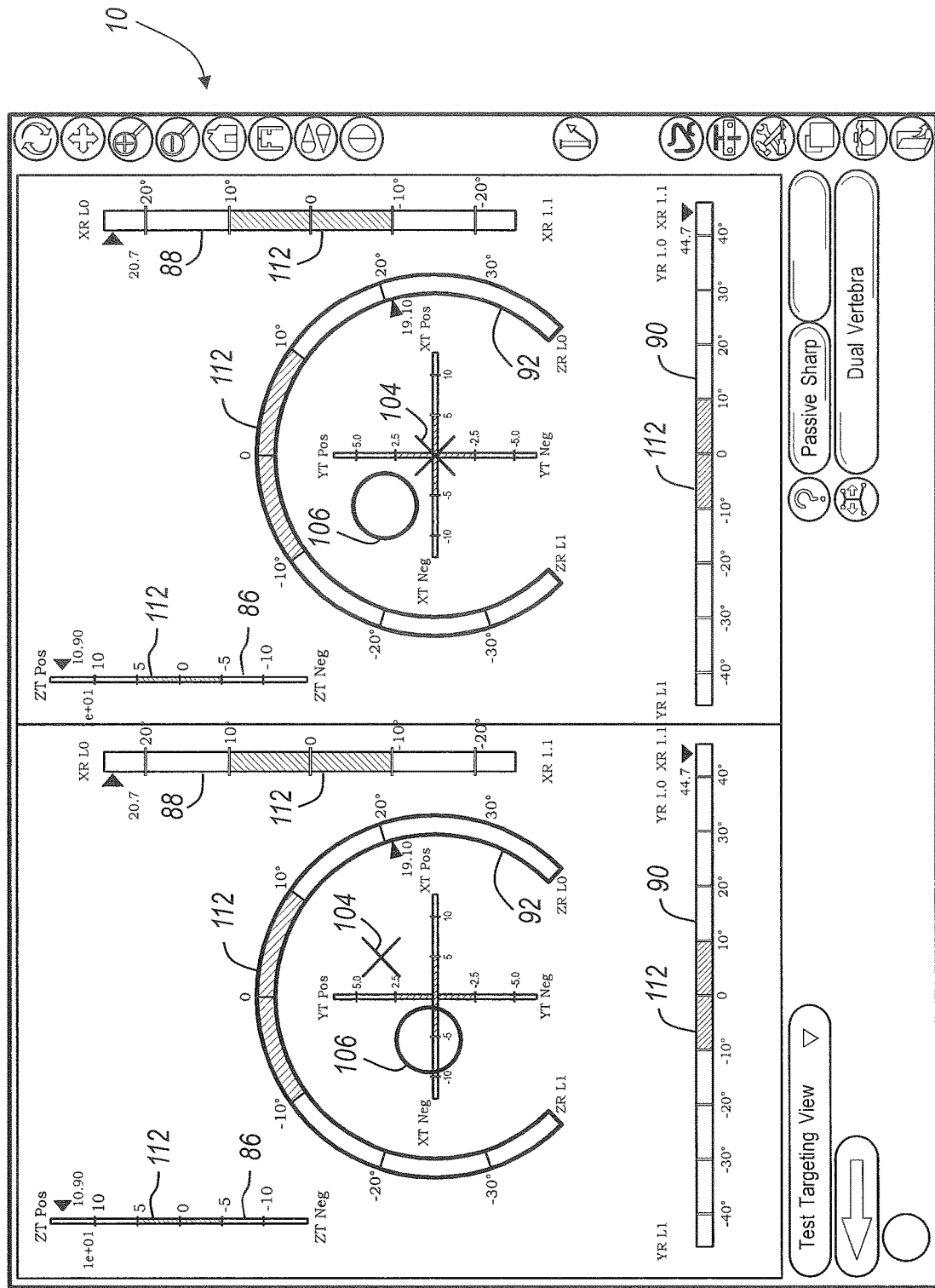
FIG. 9 is an illustration of a dual display according to the teachings of the present invention.

Turning now to FIGS. 8a-8g, another medical procedure that may employ the six degree of freedom alignment display 10 is shown in further detail, along with FIG. 9 illustrating the use of the display 10 during this medical procedure. In this example, a spinal medical procedure that implants a cervical disc implant between two vertebrae is illustrated. During this procedure, various instruments 52, as well as the implant 52 are tracked and aligned using the six degree of freedom display 10. Also, the bony structures during the procedure are also tracked.

Referring specifically to FIG. 8a, a first vertebra or vertebral body 200 is shown positioned adjacent to a second vertebra or vertebral body 202 in the cervical area of the spine. Assuming that the medical procedure is being performed in an image based system, this area of interest would be imaged by the imaging device 16. Again, a dynamic reference frame 54 may be attached to the first vertebra 200 and a second dynamic reference frame 54 may be attached to the second vertebra 202. These dynamic reference frames 54 may also be combined with tracking sensors 58, which are shown attached to the vertebral bodies 200 and 202. A center of articulation of the vertebra 200 and a center of articulation of a vertebra 202 may be identified as the targets 168 on the dual display illustrated on FIG. 9. In this way, by utilizing the center of articulation of each vertebral body with respect to each other as the targets 168, tracking of the instruments 52 used during the procedure, as well as the implant 52 with respect to these articulation centers may be achieved. This center of articulation or instantaneous center of rotation is identified as the "X" along axis Y. A plane or axis X is shown perpendicular to the longitudinal or spinal axis Y. This axis is where the implant, as well as milling should be performed or centered around.

Referring to FIG. 8b, a cam distracter instrument 204 is shown distracting the vertebra 200 relative to the vertebra 202. The cam distracter 204 may be tracked, via another tracking sensor 58 affixed to the cam distracter 204. In this way, the six degree of freedom display 10 illustrated in FIG. 9 can illustrate a location of the cam distracter 204 relative to the center of each vertebra 200 and 202 independently on the display. Since the instrument 204 is rigid, by locating the tracking sensor 58 on the instrument 204, the distal end of the instrument 204 is known and may be illustrated on the display 10 using crosshairs 104 and circle 106 to represent the tip and hind, respectively.

Once each vertebrae 200 and 202 have been distracted by the cam distracter 204, a sagittal wedge 206 also having a tracking sensor 58 is utilized and shown in FIG. 8c. The sagittal wedge 206 is used to center each vertebrae 200 and 202, along the sagittal plane and again may be tracked and displayed with six degree of freedom on the display 10, as illustrated in FIG. 9. In this regard, the surgeon can confirm both visually and via the display 10 that the sagittal wedge 206 is centered on the sagittal plane between the vertebrae 200 and 202, as well as obtain the proper depth, via the Z axis display 86 on the display 10, illustrated in FIG. 9.

Once the sagittal centering has been achieved with the sagittal wedge 206, the medical procedure proceeds to burring as shown in FIG. 8d. In this regard, a burr 208 attached to a burring hand piece 210, also having a tracking sensor 58, is used to burr an area between the first vertebra 200 and the second vertebra 202. Here again, the orientation of the burr 208 relative to each vertebra 200 and 202 may be displayed on the display 10 with six degree of freedom information. Therefore, burring along the proper X and Y plane, as well as the proper depth may be visually displayed with the appropriate indicia, as illustrated in FIG. 9. Rotational information about the corresponding X, Y and Z axes is also displayed. By burring within the safe zones 112 using the information regarding the surgical implant 52 as the safe zones 112, the surgeon can be assured to perform the proper burring between the vertebrae 200 and 202 to insure a proper oriented fit for the surgical implant 52. By tracking the burr 208 with six degrees of freedom information, the mounting anchors 212 for the hand piece 210 are optional and may not be required. Additionally, each single display in the dual display 10, as shown in FIG. 9, may also superimpose an image of each vertebrae 200 and 202 relative to one another on the display with each display having its coordinate system referenced to one of the vertebrae. The resulting milled vertebrae 200 and 202 are shown in FIG. 8e with a ring portion 214 milled to receive the spinal implant 52.

Referring to FIGS. 8f and 8g, the spinal implant 52 is shown being implanted between the vertebrae 200 and 202 using an implant inserter 216 that is also tracked by tracking sensor 58. The spinal implant 52 may be any type of cervical or other spinal disc implant for any other area of the spine. For example, the spinal implant may be the spinal implant disclosed in U.S. Pat. No. 5,674,296, entitled "Human Spinal Disc Prosthesis," issued Oct. 7, 1997, U.S. Pat. No. 5,865,846, entitled "Human Spinal Disc Prosthesis," issued Feb. 2, 1999, also known as the Bryan Cervical Disc System, offered by Medtronic Sofamor Danek of Minneapolis, Minn. or the Prestige Cervical Disc System, also offered by Medtronic Sofamor Danek, or any other spinal disc implant, all of which are hereby incorporated by reference. By tracking the implant inserter 216 relative to the vertebrae 200 and 202, proper orientation of the spinal implant 52, as well as rotational orientation about the Z axis can be clearly displayed on the six degree of freedom display 10, as shown in FIG. 9. Rotation about the Z axis is used to make sure that the flanges 218 of the implant 52 are properly oriented and centered along the sagittal plane, as shown in FIG. 8g. Again, by using the display 10, as illustrated in FIG. 9, the anchors 220 are optional since orientation of the implant 52 can be tracked continuously as it is inserted between the vertebrae 200 and 202. Here again, this eliminates the need for forming holes in the vertebrae 200 and 202. It should further be noted that the implant 52 illustrated in these figures is merely an exemplary type of spinal implant and any known spinal implants may also be similarly tracked. For example, another common type of spinal implant is formed from a two-piece unit that includes a ball and cup articulating structure that may likewise be independently tracked to assure proper fit and placement.

Here again, the six degree of freedom display 10, which is illustrated as a split or dual display 10 in FIG. 9 assists a surgeon in implanting a spinal implant 52 in order to achieve proper fixation and orientation of the implant 52, relative to two movable vertebrae 200 and 202. By tracking each vertebra 200 and 202 independently, and tracking its resection, should one vertebra be resected off-plane due to anatomical anomalies, adjustment of the plane at the adjacent vertebra may be achieved in order to still provide a proper fit for the spinal implant 52. In this way, each vertebrae 200 and 202 can be independently monitored, so that if one is off axis, the other can be manipulated accordingly to account for this adjustment. Additionally, by monitoring the entire process having six degree of freedom information, via display 10, further accuracy was achieved, thereby providing increased range of motion for the patient after implantation of the implant 52.

By use of the six degree of freedom display, for the various types of medical procedures, improved results can be achieved by providing the surgeon with the necessary information required. In regard to surgical implants, the range of motion may be increased while reducing impingement of two-part articulating or fixed implants. This also enables maximum force transfer between the implant and the body. With therapy delivery procedures, by knowing the location of the catheter delivery tube and the specific port orientation, accurately aiming at the site is enabled to provide maximum delivery of the therapy at the correct site. This procedure also enhances and enables better results when using an ablation catheter by again knowing the rotational orientation of the ablation catheter and the ablation electrode relative to the area in the wall of the artery that requires ablation. Finally, by knowing the rotational orientation of a ablation or biopsy catheter, this type of catheter may be easily directed and aligned to tumors, stem cells, or other desired sites in an easy and efficient manner.

Figure 10:
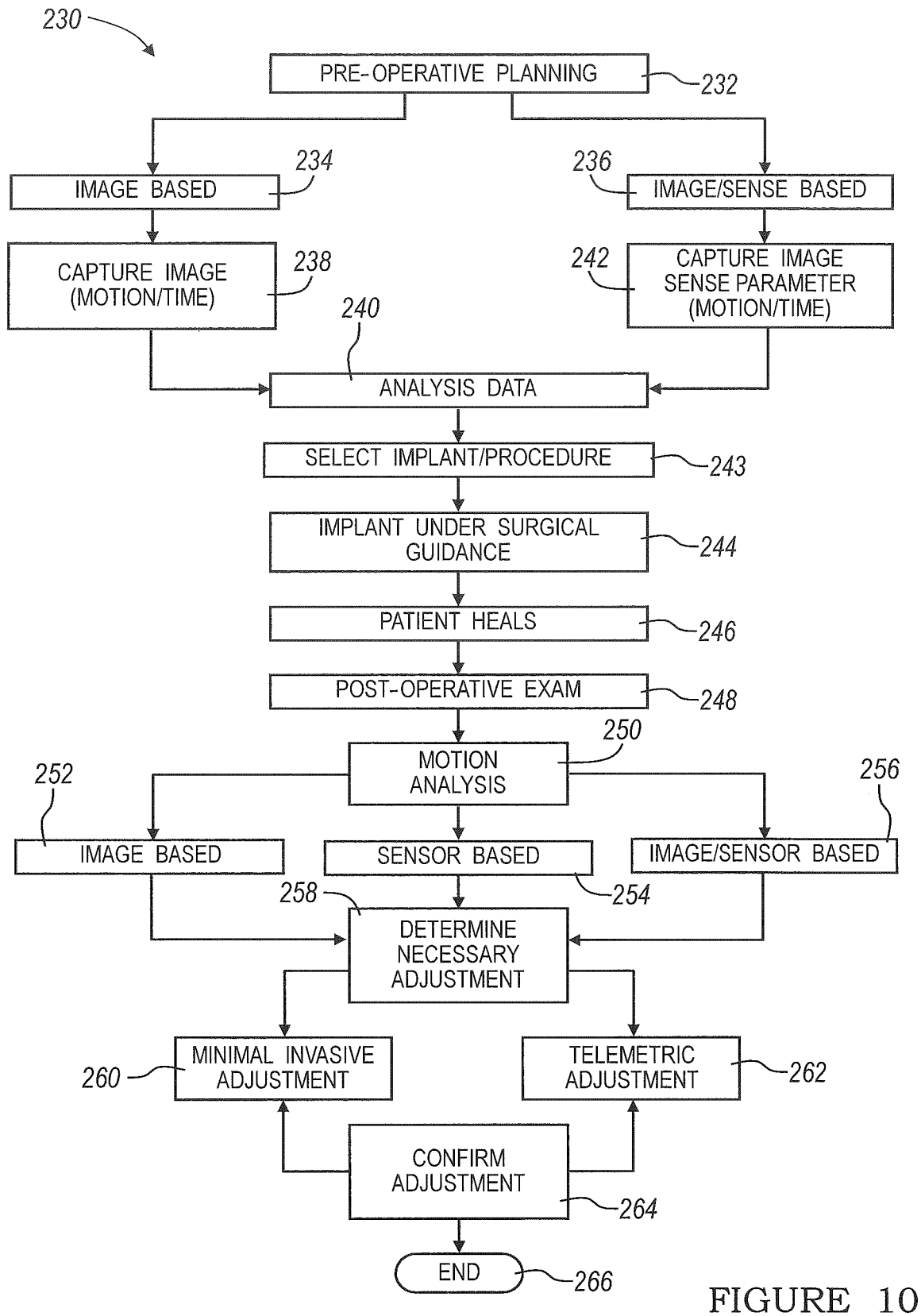
FIG. 10 is a logic block diagram illustrating a method for pre-operative planning and post-operative exam and tuning of an implant according to the teachings of the present invention.

Turning to FIG. 10, a method 230 for post-operative adjustment or tuning of implants, such as a spinal implant, according to the teachings of the present invention is disclosed. The method 230 also includes pre-operative planning, implanting, as well as the post-operative exam procedure. In this regard, the method 230 begins at block 232 where pre-operative planning of the medical procedure begins. The pre-operative planning proceeds from block 232 to either block 234 if an image based pre-operative plan is conducted or block 236 if both an image and sensing pre-operative plan is conducted. If an image based pre-operative plan is being conducted, the method proceeds to block 238 where pre-operative image data is acquired. The pre-operative images may be captured from a four-dimensional CT scan, which provides for capturing images over a specific time frame. In this regard, if the pre-operative planning is for implantation of a cervical disc, the patient may be asked to move his or her neck in different manners to capture the image data over time. Alternatively, any other type of imaging device 16 may be employed to either simply gather static image data or image data over time. The captured image data may also be used in conjunction with the electromagnetic tracking system 44, as discussed herein. Another example of pre-operative planning using a tracking system is disclosed in U.S. Pat. No. 6,470,207, entitled "Navigation Guidance Via Computer-Assisted Fluoroscopic Imaging," issued Oct. 22, 2002, which is hereby incorporated by reference. Other types of pre-operative planning using a tracking system may also be employed. This image data is then analyzed at the analysis data block 240, further discussed herein.

Should the pre-operative planning proceed to block 236, which employs the image and sense-based pre-operative planning, this procedure will capture image data and sense parameters at block 242. In this regard, the captured image data may be the same image data that is captured at block 238. In addition to the captured image data, various parameters in the area of interest may also be sensed during the pre-operative planning state. In this regard, probes or sensors maybe placed in the area of interest to sense the parameters, such as temperature, pressure, strain, and force motions. For example, in a cervical disc implant, sensors may be positioned between adjacent vertebrae of interest to measure temperature in certain areas, which may indicate friction or impingement. Likewise, strain gauges may be positioned to measure forces to identify areas having unacceptably high forces between the vertebrae. Again, this data is then analyzed at block 240.

At block 240, the data from either the image based or the image sense based pre-operative planning is analyzed. Should the data only include image data from block 238, this image data may be used to identify areas of interest, the patient size, and be used to assist in preparing the surgical plan. By viewing this data, such as 4D data, which is essentially 3D data over time or static image data, certain abnormal or irregular movements in the area of interest may be identified. These areas may be identified by visual examination, by performing finite element analysis or other known motion analysis to create a 3D model of the captured image. The finite element analysis may include calculating the instantaneous center of rotation "x" or make this determination from the image data itself. The overall shape of the spine may also be analyzed via the image data to identify and determine various force vectors on the discs of interest by analyzing the entire spine, the curvature of the spine and the articulation area of the angle of the spine relative to the ground. This information may be used to find force vectors and loading on the various regions of the vertebrae of interest. Should the sensed parameters also be used, or alternatively only be used, these sensor readings, which can be measured statically or actively while the patient is moving are utilized to again identify points of interest or potential abnormal activities by sensing parameters, such as temperature, pressure, stress, and strain in the area of interest.

Once the data has been analyzed at block 240, the procedure proceeds to block 243, where the implant and the type of procedure is selected. The implant is selected, based on the various abnormalities identified in order to enable the surgeon to resolve the noted abnormalities. The implant is selected based on various parameters, such as material selection, performance characteristics, stiffness, style or implant type and sizing. Once the type of implant has been selected, sizing of the implant may also be pre-operatively performed, based on the data captured and analyzed at block 240. Sizing may be performed using known sizing templates, which provides the surgeon with a visual means of correlating the size of the implant to the area of interest. Alternatively, various sized templates automated in software may also be included and stored within the work station 36 and superimposed in the area of interest to provide a visual indication of the sized implant to select. In addition to selecting the type and size of the implant, the type of procedure to position the implant may be determined pre-operatively.

Once the size and type of implant is selected, as well as the type of procedure, the procedure proceeds to block 244. At block 244, the selected implant is implanted generally under surgical guidance in the area of interest. For example, a cervical disc implant may be implanted, as illustrated in FIGS. 8a-8g. However, any other type of implant procedure may also be performed to position the selected implant, which may include a non-surgically guided procedure. Other exemplary types of surgically guided procedures are set out in U.S. Pat. No. 6,470,207, entitled "Navigation Guidance Via Computer-Assisted Fluoroscopic Imaging," issued Oct. 22, 2002; U.S. Pat. No. 6,434,415, entitled "System For Use in Displaying Images Of A Body Part," issued Aug. 13, 2002; and U.S. Pat. No. 5,592,939, entitled "Method and System for Navigating a Catheter Probe," issued Jan. 14, 1997, all of which are hereby incorporated by reference.

After implantation, there is a recovery period, exemplified by block 246. The recovery period will vary depending on the type of procedure, the type of implant, the patient's medical history and age, and other variables. During this period, the area of abnormality surrounding the implant may also heal and recover. For example, if a cervical disc was implanted, the muscular structure surrounding this area, which may have previously been overcompensating because of the abnormality may now have returned to a normal state. These surrounding structure changes, may affect the way the implant was positioned within the patient or the performance characteristics of the implant. In this regard, if the implant was positioned based upon abnormal surrounding structure, the implant may subsequently not provide the full range of motion as anticipated, thereby potentially resulting in further surgeries being required. Alternatively, the initially selected performance characteristics of the implant may have changed to due subsequent healing or other actions, thereby rendering the initial performance characteristics inappropriate for the current patient's condition. These performance characteristics can be any type of characteristics regarding the implant, including stiffness, actuation, loading, range of motion, etc. With the implant being an adjustable or tunable implant, corrections may be made to compensate for any subsequent anomalies observed by the surgeon. Again, the anomalies may result from healing of surrounding tissue, incorrect initial placement, changes in performance characteristics, or any other reasons. It should also be pointed out that if undesirable performance characteristics result after healing, the surrounding tissue and discs may also be damaged or deteriorate, thereby compounding recovery time and maybe requiring additional implants. This is the reason that providing the proper performance characteristics after healing is so critical.

After the patient has healed for some time, a post-operative exam is performed, exemplified at block 248. This post-operative exam may be conducted in different manners, depending upon the type of implant, the type of sensors and controls available with the implant, as well as the types of adjustments available with the implant. Some implants may have adjustment capabilities that require minimally invasive percutaneous type procedures, while other implants can be adjusted telemetrically or adaptively, as further discussed herein. The pre-operative exam may also be carried out using various types of equipment, again depending upon the capabilities of the implanted device, further discussed herein.

The pre-operative exam includes a motion analysis study, represented by block 250. This motion analysis study generally involves articulating the area of interest to determine range of motion, strength, etc. During this motion analysis study, the patient 14 is typically put through various motion testing. This testing may include various calisthenics, treadmill performance, weight lifting, gate analysis, etc. The motion analysis 250 can be performed and studied using an image-based procedure, set out at block 252, a sensor-based procedure, set out at block 254, or an image and sensor-based procedure, set out in block 256. It should also be pointed out that while block 250 is labeled motion analysis, the analysis can be performed via static image-based procedures or static sensor-based procedures, which are contemplated and included in the motion analysis study 250. In this regard, as opposed to putting the patient through various motion tests, the static image data or sensed data can be obtained and reviewed, via the image-based block 252 or the sensor-based block 254 to determine if the performance characteristics have changed. These static studies would simply look at the proper placement, impingement, etc. in the areas of interest to be used for subsequent post-operative tuning, further discussed herein.

The image-based procedure may be performed by either employing a localization or navigation tracking system or capturing image data, such as 3D or 4D image data, by an imaging device, such as a 4D CT imaging device. Should the motion analysis study be performed using localization or navigation technology, capturing image data and registration is performed as disclosed herein. U.S. Pat. No. 6,434,415, entitled "System for Use in Displaying Images of a Body Part," issued Aug. 13, 2002, also discloses pre-operative planning using navigation technology, which is hereby incorporated by reference. In general, pre-acquired image data may be obtained, for example, in the cervical spinal region. Before this image data is obtained, fiducial markers and localization sensors may be attached to each vertebrae of interest. Once the image data has been captured with these sensors in place, the patient 14 may be positioned on a treadmill with the tracking system 44 placed in proximity to track the motion of each vertebrae. This motion can include a gate analysis study of the patient's motion as well. Before the motion analysis begins, the navigation space of the patient 14 is registered to the pre-acquired images. Once the patient 14 begins the motion or movement for the motion analysis 250, tracking of the moving vertebrae may be captured and illustrated on a display, such as the display 10, or any other display.

If localization and navigation technology is not employed, image data may simply be captured over time during the motion analysis 250, for example, by the use of a four-dimensional CT scan. With this image data captured, each individual vertebrae may be segmented out using known segmenting algorithms. These types of algorithms generally involve thresholding or templates, which will segment out each vertebra in the scan. Once each vertebrae is segmented out, finite element analysis may be performed using known finite element analysis. The finite element analysis may also be used to calculate the instantaneous center of rotation "x". The information gathered during motion analysis 250 is used to determine the necessary adjustment of the implant at block 258. This information may include visualization of impinged areas around the implant, misalignment, etc.

Should the motion analysis be sensor-based, as illustrated at block 254, the sensor readings of various parameters are used to determine if there is any necessary adjustment, at block 258. The sensor based approach may either take readings from sensors located within the implant or from sensors attached to the patient during this analysis. The sensors may take temperature readings, which can indicate potential friction and higher forces, strain or stress readings, as well as load readings or any other parameter readings. Again, this information is used at block 258 to determine the necessary adjustment to the implant.

At block 256, both an image and sensor-based motion analysis may be conducted. This analysis essentially combines the image data at block 252 and the sensor data at block 254 to perform the post-operative analysis of the patient. Again, this information is used at block 258 to determine any necessary adjustments of the implant. When using both the image and sensor-based motion analysis, the sensed parameters may be synchronized in time with the image data to provide information on when the sensed parameters were captured relative to the time and the image.

At block 258, the data captured during motion analysis 250 is studied to determine whether any adjustments are necessary relative to the implant. For example, if a cervical disc was implanted and the patient healed and subsequent spinal alignment occurred, the range of motion may be compromised. In order to provide the proper range of motion, post-operative tuning of the implant may be necessary, based on the motion analysis study 250.

The post-operative tuning of the implant may also be necessary when the performance characteristics of the implant have changed. Performance characteristics may be selected, based on various criteria, such as when the patient is in a relatively static state, thus requiring certain performance characteristics, as compared to when the patient is in vigorous active state, where the performance characteristics must be changed. For example, the spinal implant may not need significant stiffness in a relatively static condition, while in very active condition, the spinal implant may require a stiffer cushioning. The performance characteristic may have been selected when the patient was disabled, so that once the patient heals, the performance characteristics may have to be adjusted accordingly. This adjustment may be conducted using a minimally invasive adjustment procedure at block 260 or a telemetric adjustment procedure at block 262.

In the minimally invasive adjustment at block 260, percutaneous adjustment of the implant may be performed by actuating various adjustment mechanisms within the implant, further discussed herein. For example, adjustment screws may be positioned at hinge points within the implant and engaged by a driver in a minimally invasive type procedure to provide the proper adjustment, thereby reacquiring the proper range of motion, via adjusting the articulating surfaces of the implant. Adjustment of the performance characteristic, such as stiffness may also be performed, as further discussed herein.

Should a telemetric adjustment procedure be performed at block 262, a non-surgical adjustment would be performed. In this regard, the implant may be driven telemetrically, using known telemetric type wireless systems, such as that disclosed in U.S. Pat. No. 6,474,341, entitled "Surgical Communication Power System," issued Nov. 5, 2002, which is hereby incorporated by reference or any other known wireless telemetric systems. The telemetric system may be an RF based or electromagnetic based telemetric system, as is known in the art. The implant may be a passive or active battery powered device that includes motors, pumps or any other devices used to adjust the implant, further discussed herein.

Once the adjustments have been performed, the procedure proceeds to block 264 where the adjustment is confirmed. If the adjustment is proper, the procedure ends at block 266. If not, further adjustments are performed. This pre-operative and post-operative procedure provides better initial implantation accuracy and implant selection, as well as the opportunity for post-operative tuning or adjustment of the implant. The post-operative tuning enables adjustment of articulating surfaces, supports, or other parameters within the implant post-operatively without requiring revision surgery.

Figure 11:
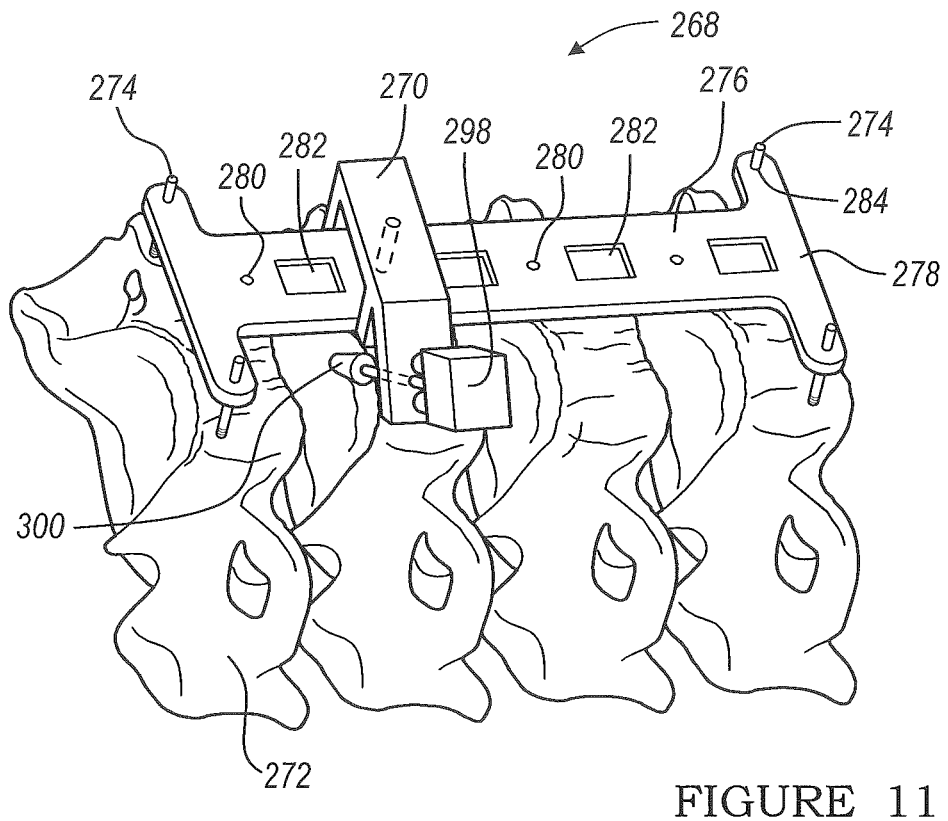
FIG. 11 is a perspective view of a platform and jig used in a minimally invasive surgical navigation spinal procedure.
Figure 12:
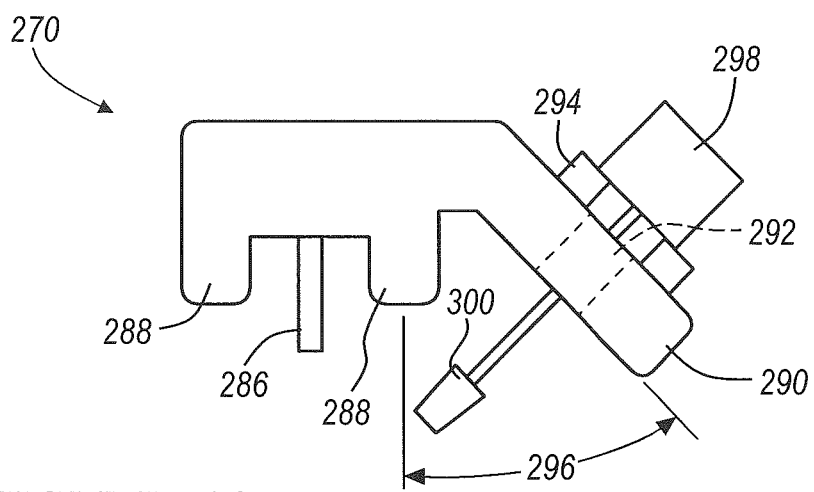
FIG. 12 is a perspective view of the jig that is operable to be attached to the platform of FIG. 11.

Referring to FIGS. 11 and 12, an instrument assembly that includes a mounting platform 268 and an attachment jig 270 for use in a surgical navigated spinal procedure is illustrated. The mounting platform 268 is percutaneously attached to a series of vertebrae 272, via multiple K-wires 274. In this regard, the mounting platform 268 is positioned outside the patient's body and above the vertebrae 272 of interest. The mounting platform 268 may be sized to span any number of vertebrae 272. In this example, four vertebrae 272 are spanned with the mounting platform 268 with the first and fourth vertebrae being secured to the mounting platform, via K-wires 274. The mounting platform 268 is designed to retain the spanned or captured vertebrae 272 in a relatively fixed or rigid manner during the spinal disc implant procedure. With the first and last vertebrae captured via the K-wires, the intermediate vertebrae 272 are generally held in a substantially fixed manner. Upon removing cartilage and other intermediate material between adjacent vertebrae, additional K-wires may be necessary for the intermediate vertebrae 272 to maintain the rigid structure.

The mounting platform 268 generally includes a rectangular-shaped beam 276 and a pair of outer attachment members 278. The rectangular beam 276 defines a plurality of peg holes 280, which are used to adjustably and removably retain the jig 270, along the member 276. The rectangular beam 276 also defines access and viewing holes or ports 282 enabling access from above and viewing of the relevant vertebrae. These access windows 282 can also be used to receive or pass surgical instruments during the medical procedure. Each attachment member 276 defines K-wire holes 284, which slidably receive the K-wires 274 in order to retain and secure the mounting platform 268 relative to the vertebrae 272.

An exemplary positioning jig 270 is illustrated in further detail in FIG. 12 and is operable to be removably attached to the mounting platform 268, as shown in FIG. 11. In this regard, the jig 270 includes attachment peg 286 that is slidably received within holes 280. Positioned adjacent to the peg 286 is a pair of shoulders 288 that extend on either side of the rectangular beam 276 as the peg 286 is received within the hole 280. The jig 270 may be positioned along any part of the rectangular beam 276 by simply slidably inserting the peg 286 into one of the selected holes 280. Alternatively, any type of attachment mechanism to attach the jig 270 to the mounting platform 268 may be used. Once the peg 286 is positioned in one of the selected holes 280, the jig 270 is positioned substantially between a pair of vertebrae 272 in which the surgical procedure will be performed. The jig 270 further includes a work platform 290 that defines a passage 292 and includes a securing mechanism 294. The work platform 290 is positioned at an angle relative to the mounting platform 268 to provide intervertebral body access. The angle 296 illustrated with jig 270 provides for a 45° working platform 290. It should also be pointed out that multiple jigs 270 may be provided with the working platform 290 being positioned at various angles or the jig 270 may be adjustable to vary the angle, via a hinge or an adjustment mechanism between the working platform and the body of the jig 270.

The working platform 290 enables various instruments to be attached to the working platform, via the attachment mechanism 294, which may be a screw attachment, quick lock attachment, snap-fit attachment, or any other type of attachment mechanism. In one embodiment, a robot 298 may be attached to the working platform 290. This robot 298 may be remotely controlled and be used to drive milling, drilling, resection, or other instruments 300 through the passage 292. The robot 298 can either actuate the motor for the instrument 300 or can simply provide and act as an adjustable guide tube that may be controlled directly or remotely. Any type of known robotically controlled instrument may be utilized. Alternatively, the jig 270 may retain a manually adjustable guide tube that receives various instruments to be used during the procedure. The adjustable guide tube may also be lockable into a desired position in order to provide a rigid guide tube. Still further, the jig 270 may simply be used to pass and guide various instruments between the vertebral bodies 272. In this regard, the instruments as illustrated in FIGS. 8a-8g may be used in accordance with the jig 270 or other jigs providing various types of access ports 292. These access ports may be circular, slotted or any other shaped port to enable access between the vertebral bodies 272.

Generally, the mounting platform 268 will not include any localization sensors 58 or fiducial markers 60. The localization sensors 58 are generally positioned relative to the jig 270. The localization sensors 58 may be positioned on the guide tube and on the surgical instrument to determine orientation and depth of the surgical instrument 300, respectively. The localization sensor 58 may also be positioned on the robotically controlled device 298 to determine both orientation and depth of the instrument 300. The mounting platform 268 may also include localization sensors 58 if desired, which may be used to provide further localization of the vertebrae 272. It should further be pointed out that the dynamic reference frame 54 may be attached or integrated into the mounting platform 268 in order to provide increased accuracy during the implant procedure. In this regard, since any motion of the mounting platform 268 would be identified, via an integrated dynamic reference frame 54, this motion is positioned substantially adjacent to the area of interest and the area being operated upon, providing increased registration and tracking of the instruments during the procedure.

By providing the mounting platform 268 that spans multiple vertebrae, multiple segment implantation may be performed in a minimally invasive and surgical navigated manner between the multiple vertebrae 272. For example, as illustrated, three separate cervical discs may be positioned between the four vertebrae 272 without requiring removal or replacement of multiple jigs as would typically be necessary. By providing a mounting platform 268 that can accommodate various size jigs and can be positioned between various vertebrae 272, a more precise and accurate implantation may be achieved in a more minimally invasive and efficient manner.

Figure 13:
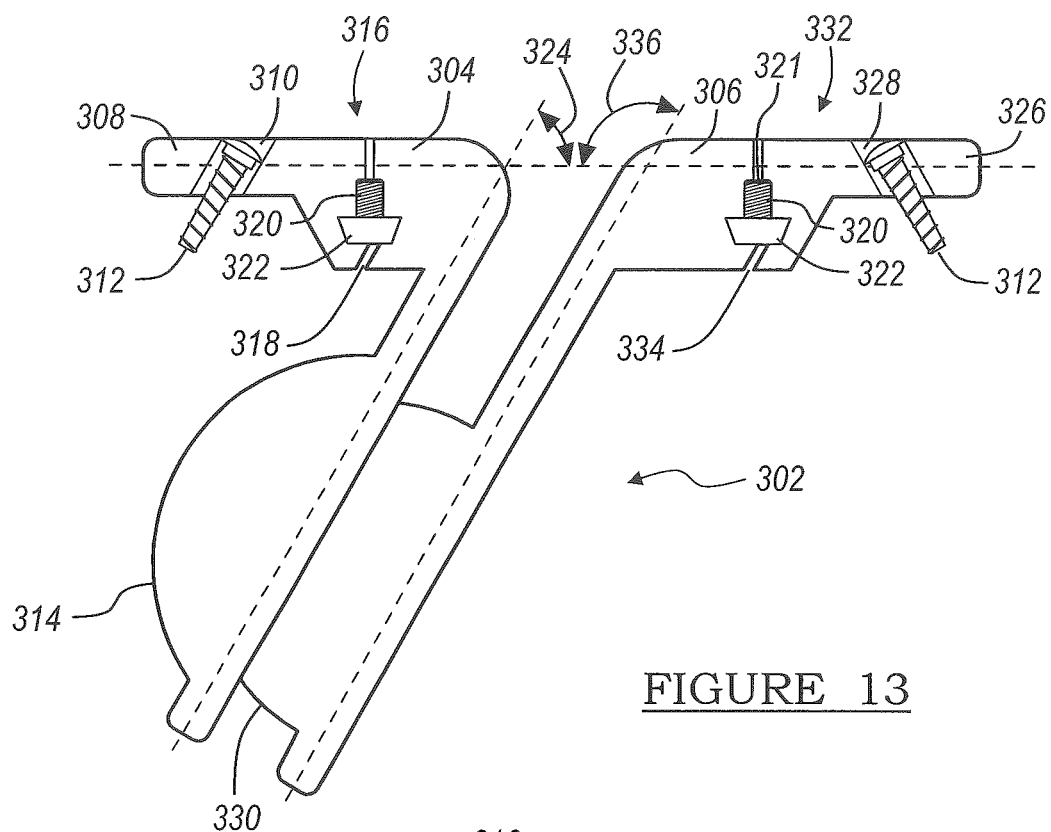
FIG. 13 is a side view of a cervical disc implant having a minimally invasive adjustment mechanism.

A ball and socket type cervical disc implant 302 is illustrated in FIG. 13 that provides for percutaneous adjustment. The cervical disc implant 302 is based upon the Prestige Cervical Disc System provided by Medtronic Sofamor Danek of Minneapolis, Minn., but includes a tuning or adjustment capability. It should also be pointed out that while a cervical disc implant is disclosed herein, the present invention is not limited to merely cervical disc implants, but may include thoracic and lumbar spinal implants, as well as any other type of orthopedic implant that may require post-operative tuning. The cervical disc 302 comprises two articulating members that include a socket member 304 and a ball member 306. The socket member 304 includes a mounting flange 308 that defines generally two mounting holes 310 for receiving bone screws 312. The socket member 304 also defines the articulating socket 314 and is generally placed at an angle relative to the flange 308. Located at the junction between the flange 308 and the socket 314 is an adjustment or hinge region 316 defining an adjustment slot 318. Located within the adjustment slot 318 is an adjustment screw 320. Upon percutaneously engaging a head 321 of the adjustment screw 320, via any known driving instrument, the angle 324 between the flange and the socket 314 may be adjusted, via a wedge portion 322, in a minimally invasive manner. The head 321 may include a hex, a Phillips, a slotted, or any other type of engagable drive mechanisms that can be engaged by any type of instrument. Moreover, the adjustment screw 320 may be reversed so that the head 321 is located opposite, at 90°, or at any other orientation other than as illustrated to provide a different access point for the head 321.

The ball member 306 also includes a flange 326 defining screw holes 328 to receive bone screws 312. The ball member 306 also includes an articulating ball or spherical surface 330 that articulates with the socket 314. The flange 306 also includes adjustment or tuning portion 332 that defines a slot 334 for receiving another set screw 320 having head 322. Again, upon adjustment of the set screw 320, the angle 336 between the flange 326 and the ball 330 is adjusted in a minimally invasive manner, via percutaneous placement of a surgical driver that engages the head 321 of the adjustment screw 320.

By providing tuning or adjustment portions 316 and 332 relative to the ball 330 and socket 314, adjustment of the articulating ball 330 relative to the socket 314 may be made. Again, after a motion analysis 250 has been performed, a minimally invasive adjustment of the implant 302, such as the implant shown in FIG. 13 may be performed by simply adjusting set screws 320. This adjustment may relieve impingement, increase range of motion, or provide other post-operative adjustments that would previously require a revision type surgical procedure.

Figure 14:
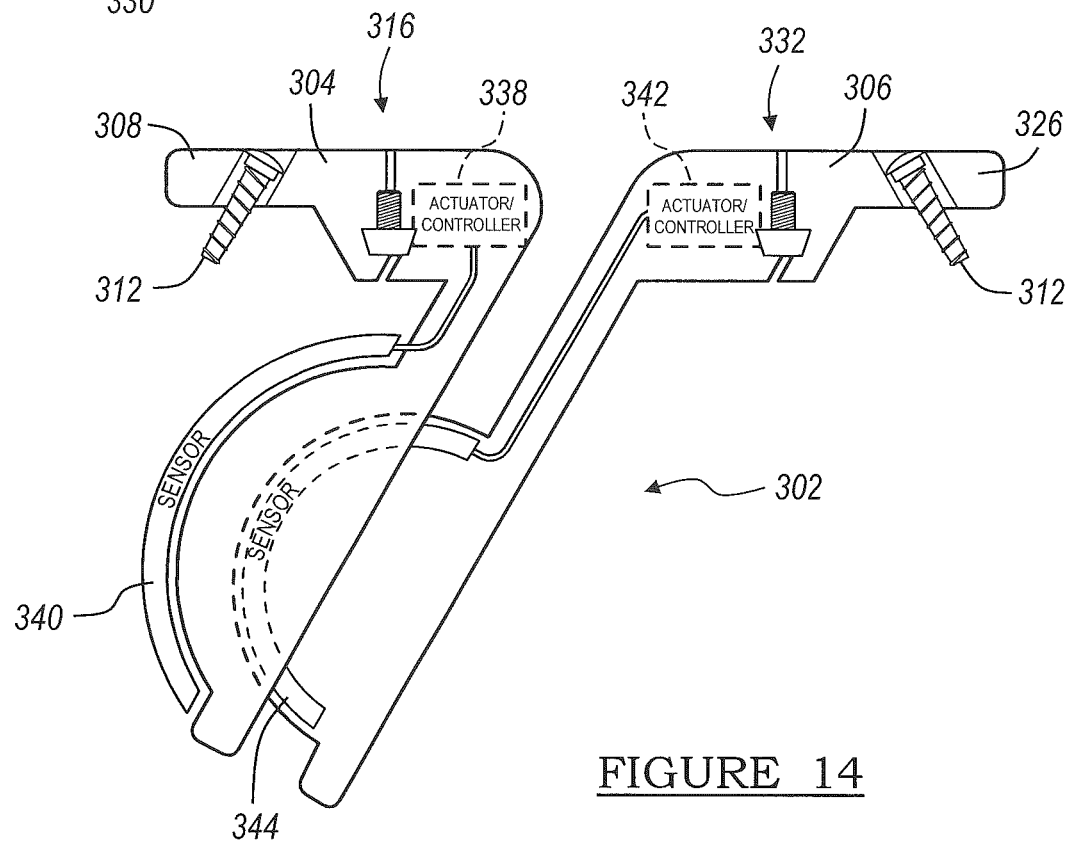
FIG. 14 is a side view of a cervical disc implant having a telemetric adjustment mechanism.

Referring now to FIG. 14, a modified embodiment of the cervical disc 302 is illustrated. In this regard, like reference numerals will be used to identify like structures as shown in FIG. 13. The implant 302 provides for a telemetric type adjustment, as well as telemetric sensing capabilities. In this regard, the socket member 304 includes an actuator/controller 338 and a sensor 340 positioned along the articulating surface of the socket 314. Likewise, the ball member 306 also includes an actuator/controller 342 and a sensor 344 positioned along the articulating ball surface 330. The sensors 340 and 344 may be used to sense various parameters in the articulating joint, including temperature, pressure, stresses, strain and other loading properties. These sensors 340 and 344 may be used during the sensor based motion analysis 254 to sense the noted parameters during the motion analysis study 250. This sensed information is sent to its corresponding actuator/controller 338 or 342, which is able to telemetrically transmit information, further discussed herein, during this sensor based motion analysis 354.

Each actuator/controller 338 and 342 may either be a passive type device or an active rechargeable battery powered device. If the actuator/controllers 338 and 342 are passive type devices, they may include resonant LC circuits, which will resonate when adjacent generating coils, generate an electromagnetic field, thereby enabling transmission of the sensed information from sensors 340 and 344. An example of such a system is set out in U.S. Pat. No. 6,474,341, entitled "Surgical Communication and Power System," issued Nov. 5, 2002, which is hereby incorporated by reference. Other types of known wireless telemetric systems may also be utilized. Actuator/controllers 338 and 342 may also be battery powered using rechargeable batteries that are either embedded within the implant or positioned remote from the implant and implanted within the patient, similar to known pacemaker technology. These rechargeable batteries may be recharged telemetrically similar to existing pacemaker batteries, as is known in the art.

Figure 15:
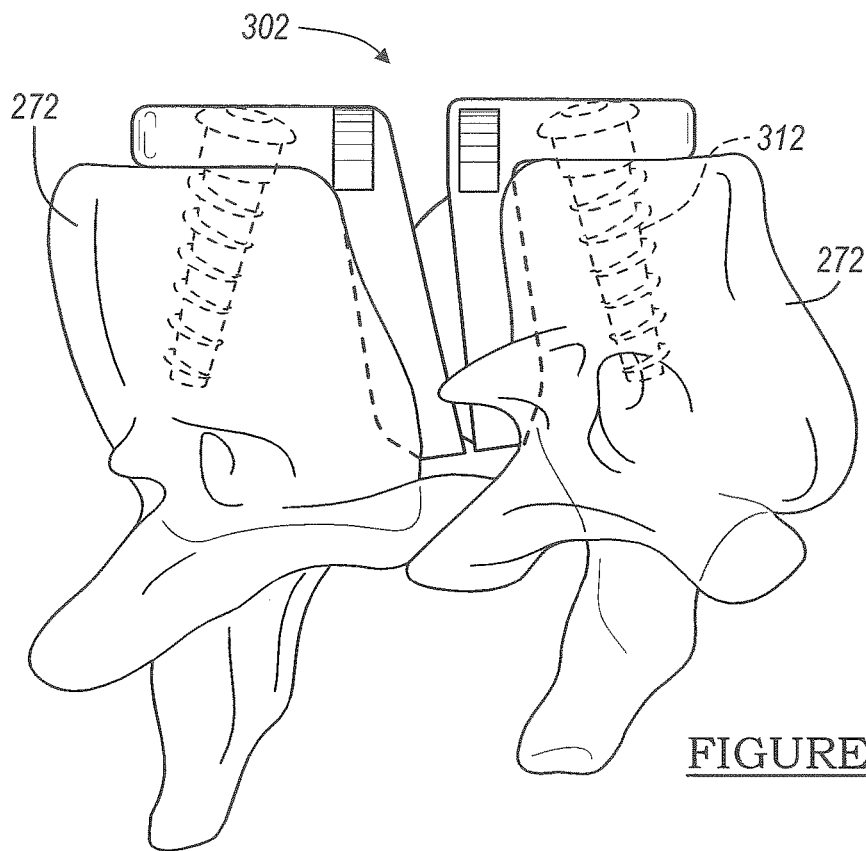
FIG. 15 illustrates an implant of FIGS. 14 and 15 implanted into a spine.

If the system is a passive system, the data may be acquired from the corresponding sensor during the motion analysis study 250 in the post-operative exam 248 during the various motion tests performed on the patient 14. This information is gathered at the time of the study and is used to analyze whether or not further adjustments are necessary to the implant 302. Alternatively, if the system is an active system and battery powered, data may be sampled over time, stored in memory and transferred during the motion analysis study 250 or during other transfer periods, as further discussed herein. With this type of telemetric system, the implant 302 may be adjusted remotely by driving either actuator/controller 338 or 342 to remotely adjust the adjustable set screw 320, via known actuation type mechanisms. Again, while a hinge/set screw adjustment mechanism is shown, any other appropriate adjustment mechanism may be employed, such as worm gears, pinions, etc. Thus, telemetric adjustment 262 may be performed by simply positioning a corresponding transmit and receiving instrument adjacent to the implant site to both receive sensor information and remotely drive the actuators/controllers 338 and 342 to provide remote telemetric adjustment of the implant in a non-surgical manner. By adjusting either the angle 324 or the angle 336, the range of motion, contact, articulating surface adjustments, or other type of adjustments to relieve impingement and increase the range of motion may be performed in a post tuning technique. Briefly, FIG. 15 shows the implant 302 implanted between a pair of vertebrae 272 and aligned, such that the instantaneous center of rotation are properly positioned within the center articulating longitudinal axis Y of the spine (see FIG. 8a).

Figure 16:
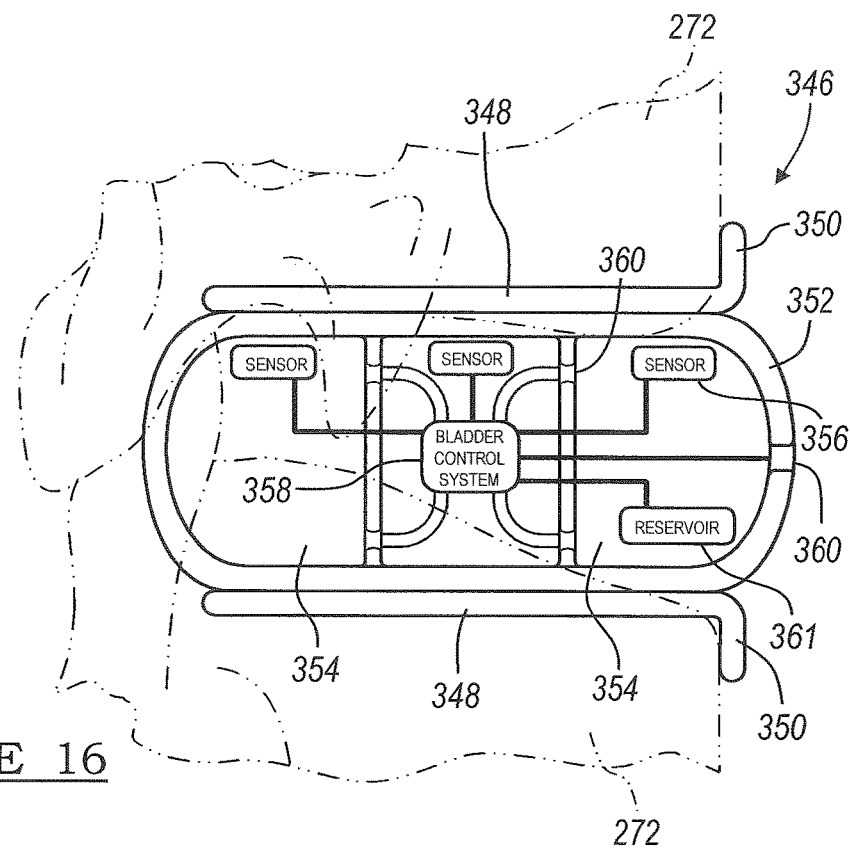
FIG. 16 is a side cross-sectional view of a cervical disc implant according to the teachings of the present invention.

Referring to FIG. 16, another embodiment of a cervical spinal implant 346 is illustrated. The spinal implant 346 is based on the spinal disc prosthesis, set out in U.S. Pat. No. 5,674,296, entitled "Human Spinal Disc Prosthesis," issued Oct. 7, 1997 and U.S. Pat. No. 5,865,846, entitled "Human Spinal Disc Prosthesis," issued Feb. 2, 1999, each of which are hereby incorporated by reference. That is also known as the "Bryan Cervical Disc System," offered by Medtronic Sofamor Danek of Minneapolis, Minn. The spinal implant 346, however, also includes a tuning and adjustment mechanism. The spinal implant includes a pair of rigid support plates 348 and a pair of attachment flanges 350 that define attachment holes to receive bone screws (see FIG. 8g). Positioned between the support plates 348 is a flexible bladder device 352.

In order to provide for either minimally invasive or telemetric adjustment of the implant 346, the bladder mechanism 352 is separated into a plurality of individual bladders 354. As illustrated, the implant 346 includes three adjacent bladders 354. Located within each bladder 354 is a sensor 356 that is used to sense the pressure within each bladder 354. These sensor readings are passed to a bladder control system 358. The bladder control system 358 may again be a passive device or an active battery powered device. If passive, the sensor information will be received during the motion analysis study 250 and adjustment may be performed telemetrically during this study using known telemetric driving devices. If the bladder control system 358 is an active powered system, the system may either operate similar to the passive system or may be an adaptive system that provides real time adjustment for the implant 346. In this regard, each sensor 356 may sense pressure differences in each bladder 354 while the bladder control system 358 attempts to equalize the pressures in the bladders 354 in a real time manner. The bladder control system 358 includes a processor controller and either a battery or known passive driving device. The bladder control system 358 also includes a pump used to transfer fluid retained within the bladders 354 by controlling remote valves 360 and a memory if necessary for storing sampled data.

The implant 346 may also include a reservoir 361 that retains a drug that may be delivered through the external valve 360 and controlled by the bladder control system 358. In this way, controlled drug delivery to the surrounding bone may also be achieved with the implant 346. The drug can include a bone morphagenic protein (BMP) that is able to increase bone density and fusion of broken bones, by delivering the BMP over time to the surrounding infected bones. This drug delivery capability of the implant 346 may be actively delivered if the system is battery-powered, or telemetrically delivered, via an active or passive device during patient exams.

In operation, the implant 346 may be used to sense pressure in each individual bladder 354, via the sensors 356 during the post-operative motion analysis 250. With this information, a surgeon can direct the bladder control system 358 to compensate for any abnormalities in pressure in the bladders 354 in order to try to achieve uniform pressure throughout the implant 346. The bladders 354 generally include a saline solution that can be transferred between bladders 354, via the bladder control system 358 and control valves 360. In addition, there is an external valve 360 that may be used to release saline fluid harmlessly into the body to relieve pressure. Alternatively, the external valve 360 may be used to receive additional fluid percutaneously in a minimally invasive way. Thus, the implant 346 may be post-operatively adjusted or tuned, depending upon the healing of the patient, post-operative trauma, or to provide further refinement and increased performance of the implant 346.

Figure 16A:
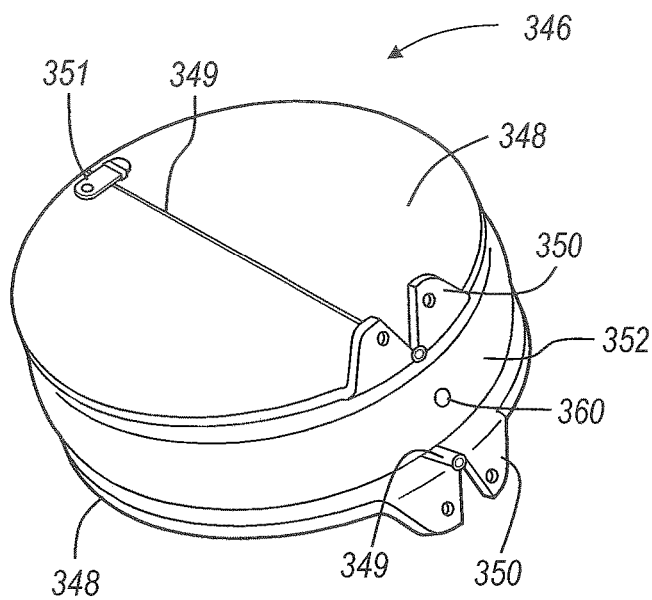
FIGS. 16a-16c are an unfolded and partially folded view of other embodiment of a cervical disc implant according to the teachings of the present invention.
Figure 16B:
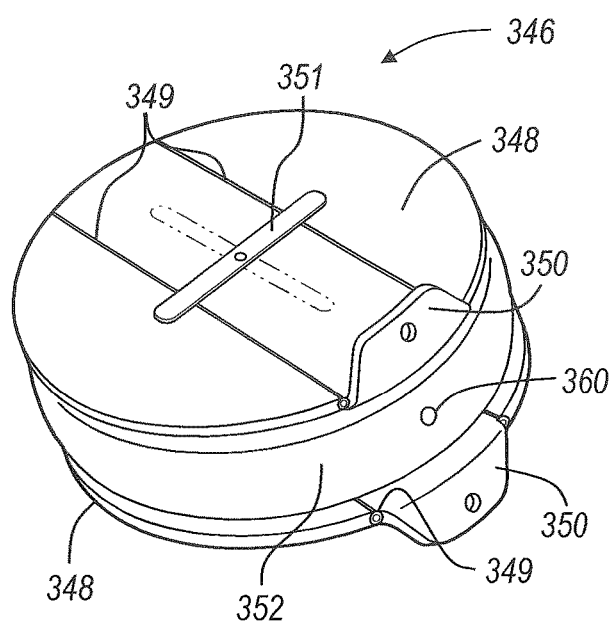
Figure 16C:
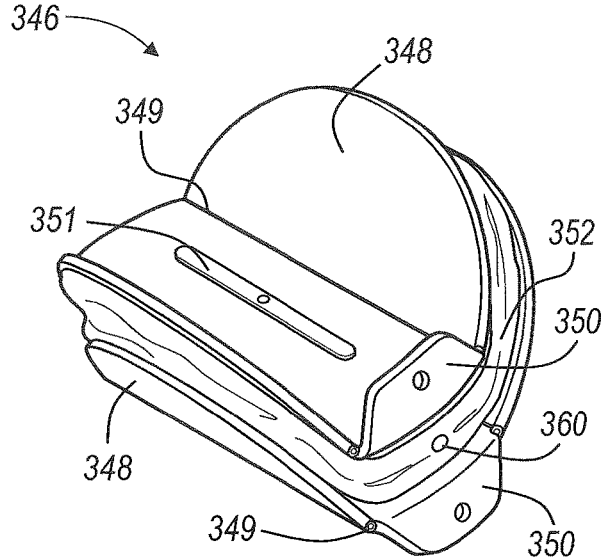

Alternate embodiments of the implant 346 is illustrated in 16a-16c. Here again, like reference numerals are used to identify like structures. The spinal implant 346 is substantially similar to the spinal implant illustrated in FIG. 16, except that the spinal implants illustrated in FIG. 16a-16c are multi-segment implants 346 that allow for a minimally invasive technique and a posterior implantation approach. The implant 346 illustrated in FIG. 16a includes a pair of rigid support plates 348 that include a hinged region 349. This hinged region 369 includes a single hinge that enables the implant 346 to be substantially compressed so that the plates 348 are adjacent to one another. Once adjacent to one another, the plates 348 may be folded via the hinge region 349 creating a semi-circular shape that is significantly smaller than the whole implant 346. This enables the implant to be implanted posteriorly in a minimally invasive manner by simply sliding the folded implant 346 into a small incision and re-assembling or unfolding the implant 346, along the hinge region 349 at the implant area. The hinge 349 also includes a lock 351 that is used to lock the hinge 349 to insure that each plate 348 is locked in a planar fashion. Once locked, the implant 346 is positioned between the adjacent vertebrae 242 similar to that shown in FIG. 16.

Implant 346, illustrated in FIGS. 16b and 16c also includes a hinged region 349 that consists of a pair of hinges positioned on either side of the flange 350. Again, the hinge region 349 enables the end plates 348 to be folded, as illustrated in FIG. 16c to enable a posterior minimally invasive procedure. This implant 346 also includes a lock 351 that rotates to lock the pair of hinges in the hinge region 349 in a substantially planar manner.

Figure 17:
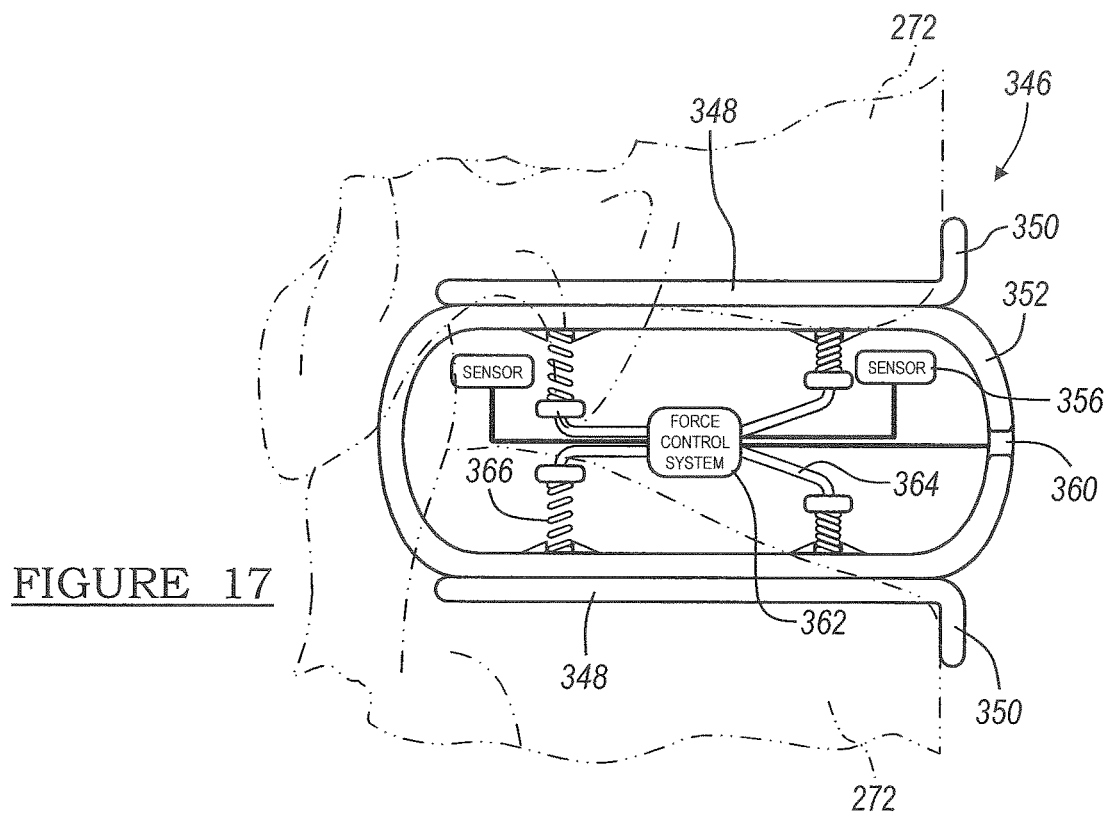
FIG. 17 is a side cross-sectional view of another cervical disc implant according to the teachings of the present invention.

Another embodiment of the spinal implant 346 is shown in FIG. 17, which provides a different type of adjustment mechanism. Here again, like reference numerals will be used to identify like structures. Again, the spinal implant 346 includes a pair of supporting plates 348, a pair of flanges 350 and a support or bladder device 352. Located within the bladder device 352 is a single bladder 354, which can be filled with a saline solution, or optionally not filled with fluid. Again, sensors 356 are located in different regions within the bladder 352 and used to either sense fluid pressure or used as a strain gauge to measure loading forces. The readings from the sensors 356 are read by a force control system 362, which can again either be a passive device or a battery powered active device. The force control system 362 operate similar to the bladder control system 358, except that as opposed to directing fluid between various bladder chambers, it includes force control beams or members 364 that are used to apply a force to the plurality of springs 366 positioned within the bladder 354. By compressing the springs 366 in different quadrants with the control beams 364, tension in the springs 366 are increased, thereby providing additional support within the implant 346. Each spring may be selectively adjusted, depending upon the desired tuning or adjustment necessary. Again, this adjustment is based upon the motion analysis study done during the post-operative exam 248.

The force control system 362 may be used to adaptively or actively adjust the implant 346 if the force control system is an active battery powered system. Alternatively, the force control system 362 may adjust the force within the implant 346 during the telemetric adjustment 262 if the system is simply passive. The bladder control system 358 and the force control system 362 may be formed using conventional micro electronics and mechanical devices or may be formed from micro electromechanical system (MEMS) technology, known in the art.

Figure 18:
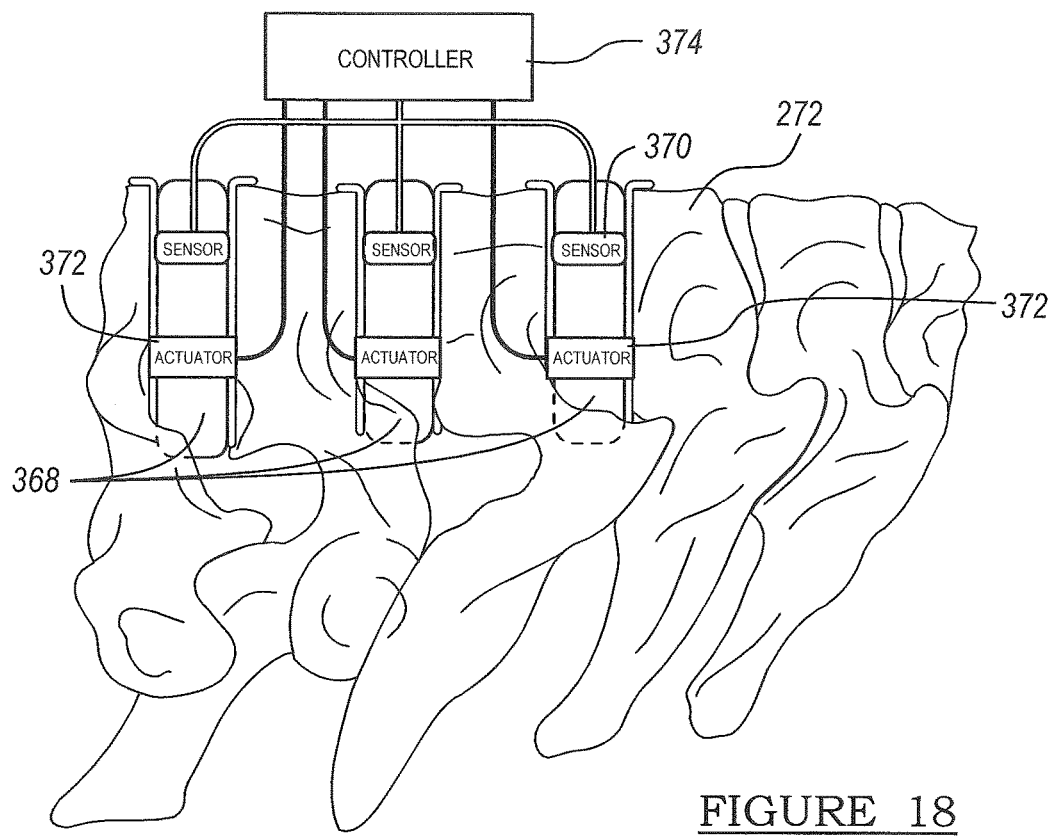
FIG. 18 illustrates a cervical disc system employing multiple cervical disc implants according to the teachings of the present invention.

A multiple segment implantation is illustrated in FIG. 18 that includes multiple implants 368. Each implant 368 may be implanted utilizing the mounting platform 268 and jig 270, as illustrated in FIGS. 11 and 12. Implants 368 may also be implanted using other procedures, such as that shown in FIGS. 8a-8g. Each implant 368 includes a sensor 370 and an adjustment actuator 372, similar to that shown in FIGS. 14, 16, and 17. However, each implant 368 is controlled and actuated, via an active rechargeable battery powered external controller 374. Optionally, each implant 368 may include its own individual internal controller 374 that can communicate to the other implants 368, via a wireless or wire connection. Alternatively, a single internal master controller 374 may be positioned within one of the implants 368, which is used to control and drive the remaining implants 368 in a master/slave relationship.

Controller 374 is used to sense various parameters again, such as temperature, pressure, etc. where actuators 372 are used to tune or adjust each implant 368 accordingly. The controller 374 may be implanted adjacent to the spinal region, similar to a controller and battery for a pacemaker. The multiple segment implantation with each implant 368 communicating with the other surrounding implants 368 enable real time adaptive control of this spinal region, such as the cervical spinal region of the patient 14. In other words, the controller 374 may sense, via the sensors 370 whether any one of the implants 368 is under too much pressure or one may be too laxed and adjust accordingly, depending upon the patient's movements. In this regard, when the patients at rest, extra support between the vertebrae 272 may not be necessary. However, when the patient 14 is doing physical activities or exercise, additional support may be necessary between each vertebrae 272 and each implant 368 may be expanded during this period in an adaptive manner. Alternatively, the controller may again simply be a passive controller or an active controller and used to send and receive information, as well as adjust the implants 368 during the post-operative exam 248, via the telemetric adjustment 262.

Figure 19:
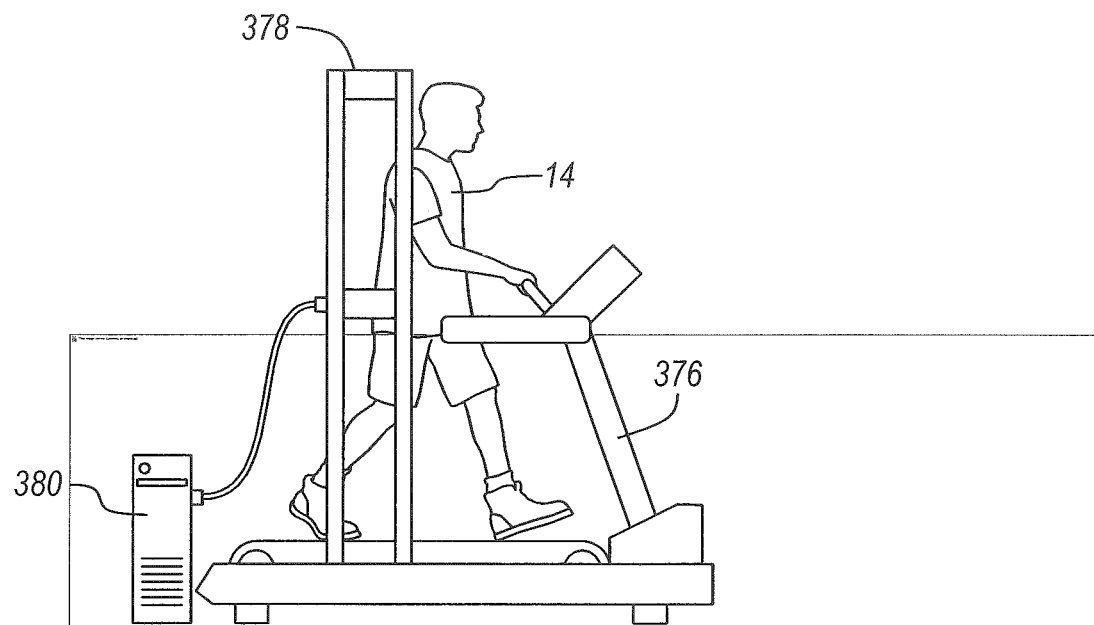
FIG. 19 illustrates a transmit/receive module used during the motion analysis study of a patient according to the teachings of the present invention.

Turning to FIG. 19, an exemplary telemetric system used for performing the motion analysis 250 is illustrated. In this regard, the patient 14 may undergo the motion analysis 250 by exercising on a treadmill 376. The treadmill 376 is positioned within a transmit/receive module 378. When the patient 14 is positioned within the transmit/receive module 378 and exercising on the treadmill 376, information can be collected from the particular implant during the motion analysis 250 using the sensor based 252 data analysis, via the telemetric adjustment 262. In other words, the transmitter/receive module 378 includes signal transmitters and receivers to either actuate a passive or active controller to receive sensed information. This information is forwarded to a control processor 380 where the surgeon can analyze the collected sensed data. Once the data has been analyzed, the controller 380 is used to actuate the transmit/receive module 378 to adjust one or more implants in the patient, via the control actuator circuits, disclosed above. It should also be noted that an imaging device may also be positioned adjacent to the patient 14 while the patient is on the treadmill 376 to provide both an image-based and a sensed-based motion analysis 250, as previously discussed.

Figure 20:
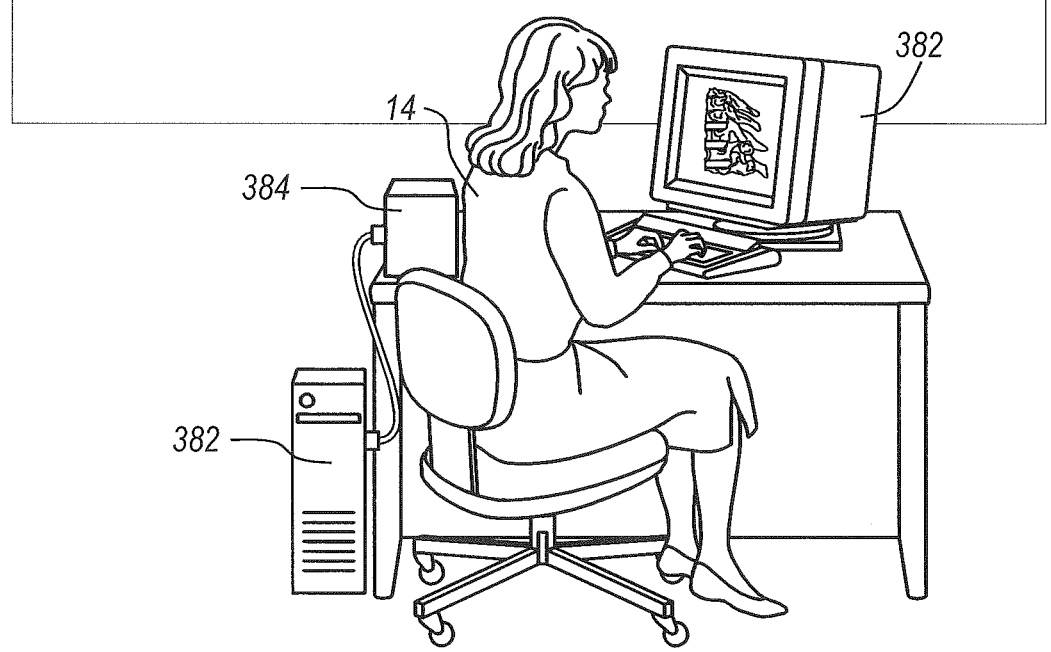
FIG. 20 illustrates a home based transmit/receive module used for a motion analysis study according to the teachings of the present invention.

Referring now to FIG. 20, another telemetric system used to transmit motion analysis information to the doctor is disclosed. With this technique, the patient 14 can simply conduct a self analysis by positioning him or herself adjacent to a computer 382. Attached to the computer 382 is a transmit/receive module 384. The transmit receive module 384 operates similar to the transmit receive module 378, except that the patient 14 can simply run through a set of suggested motions, while the transmit receive module 382 telemetrically receives information from the implant positioned within the patient 14. This information can be transmitted, via the computer 382 online to a receiving hospital or doctor's office. The doctor may then analyze this information, make a recommendation to the patient 14 whether the patient 14 should come in to the office for a telemetric adjustment 362 of the patient's implant. Alternatively, the doctor may also simply instruct the transmit control module 384, via the computer 382, to perform the telemetric adjustment of the patient 14 in the patient's home.

The procedure 230, as well as the associated implants, systems and instruments, enables both pre-operative and post-operative review and analysis. Additionally, post-operative tuning of the implant may also be achieved without requiring revision surgery or highly invasive types of procedures. In this regard, either minimally invasive or telemetric adjustments of the implants may be achieved.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A navigation system for use in guiding a medical device in a patient during a medical procedure, comprising:
    a tracking sensor configured to receive a tracking signal to be used to track and determine a position of the medical device;
    a tracking device configured to generate the tracking signal to track the medical device with the tracking sensor and to update the determined position of the medical device as the medical device is guided; and
    a work station having a display, the work station configured to provide information data to display on the display including,
    an image data of the patient along an x-axis plane, an image data of the patient along a y-axis plane, and an image data of the patient along a z-axis plane;
    safe zones used for determining where to navigate the medical device relative to each of the image data of the patient along the x-axis plane, the image data of the patient along the y-axis plane, and the image data of the patient along the z-axis plane; and
    x-axis, y-axis, and z-axis indicia of the determined position of the medical device relative to the image data of the patient and indicia of the safe zones based upon the tracking sensor receiving the tracking signal from the tracking device;
    wherein the indicia of the safe zones illustrate ranges relative to a planned trajectory path or a target;
    wherein the illustrated ranges are represented by at least a dimension illustrated along the x-axis indicia, the y-axis indicia, and the z-axis indicia and a rotation dimension illustrated about a corresponding rotation x-axis indicia, rotation y-axis indicia, and rotation z-axis indicia;
    wherein the x, y, and z-axis indicia and the rotation x, y, and z-axis indicia are simultaneously displayed.

2. The navigation system of claim 1, wherein the medical device is a surgical instrument.

3. The navigation system of claim 2, wherein the surgical instrument is a burring handpiece having a burr.

4. The navigation system of claim 1, wherein the tracking sensor is attached to the medical device.

5. The navigation system of claim 1, wherein said tracking sensor is selected from a group comprising an electromagnetic sensor, an optical sensor, an optical reflector, an electromagnetic transmitter, a conductive sensor, an acoustic sensor, or combinations thereof.

6. The navigation system of claim 1, wherein said tracking device is selected from a group comprising an electromagnetic tracking device, an optical tracking device, a conductive tracking device, an acoustic tracking device, or combinations thereof.

7. The navigation system of claim 1, further comprising an imaging device configured to generate the image data of a region of the patient.

8. The navigation system of claim 1, wherein the x-axis, the y-axis, and the z-axis indicia of the determined position of the medical device is displayed relative to each of the safe zones on the display by the work station.

9. The navigation system of claim 8, wherein the target is on the patient and the target is displayed relative to multiple planes and the safe zones.

10. The navigation system of claim 9, wherein the target is a desired trajectory of the medical device.

11. The navigation system of claim 1, wherein the safe zones are color coded zones represented by horizontal bars or vertical bars on the display for each x-axis plane, y-axis plane, and z-axis plane.

12. A method for navigating and displaying a medical device relative to patient image data during a medical procedure, comprising:
    displaying the patient image data on a display;
    tracking the medical device with a navigation system to determine a position of the medical device relative to the patient for display with the patient image data; and
    displaying indicia of the medical device at the determined position relative to both (i) the patient image data and (ii) separate safe zones associated with the medical image data on each of an x-axis plane, a y-axis plane, and a z-axis plane;
    wherein the indicia includes x-axis, y-axis, and a z-axis indicia and the indicia of the safe zones illustrate ranges relative to a planned trajectory path or a target;
    wherein the illustrated ranges are represented by at least a dimension illustrated along the x-axis indicia, the y-axis indicia, or and the z-axis indicia and a rotation dimension illustrated about a corresponding rotation x-axis indicia, rotation y-axis indicia, and rotation z-axis indicia;
    wherein the x, y, and z-axis indicia and the rotation x, y, and z-axis indicia are simultaneously displayed.

13. The method of claim 12, wherein tracking the medical device further includes tracking a surgical instrument relative to the patient with the navigation system.

14. The method of claim 13, wherein tracking the surgical instrument includes tracking a burring handpiece having a burr.

15. The method of claim 12, wherein the patient image data includes at least a first vertebra and a second vertebra and the medical device includes a burring handpiece having a burr.

16. The method of claim 15, further comprising burring within the safe zones.

17. The method of claim 12, further comprising color coding the safe zones associated with the medical image data.

18. The method of claim 15, further comprising tracking a position of the first and second vertebrae.

19. The method of claim 15, further comprising displaying a sagittal plane of the first and second vertebrae and indicia of the burr relative to the sagittal plane.

* * * * *

UNITED STATES PATENT AND TRADEMARK OFFICE
CERTIFICATE OF CORRECTION

PATENT NO. : 11,707,363 B2
APPLICATION NO. : 15/997178
DATED : July 25, 2023
INVENTOR(S) : Mark W. Hunter et al.

It is certified that error appears in the above-identified patent and that said Letters Patent is hereby corrected as shown below:

On the Title Page

Column 1, Related U.S. Application Data, Line 1, Delete "(60)" and insert --(63)-- therefor Page 8, Column 1, Other Publications, Line 35, Delete "framless" and insert --frameless-- therefor Page 8, Column 1, Other Publications, Line 48, Delete "Tesions" and insert --lesions-- therefor Page 8, Column 2, Other Publications, Line 62, Delete "localizationusing" and insert --localization using-- therefor Page 9, Column 1, Other Publications, Line 1, Delete "Ultrasoic" and insert --Ultrasonic-- therefor Page 9, Column 1, Other Publications, Lines 6-7, Delete "andComputer-Assisted Surgery,Grenoble," and insert --and Computer-Assisted Surgery, Grenoble,-- therefor Page 9, Column 1, Other Publications, Line 14, Delete "ComputerAssisted" and insert --"Computer Assisted-- therefor Page 9, Column 1, Other Publications, Line 23, Delete "22004." and insert --2004.-- therefor Page 9, Column 2, Other Publications, Line 30, Delete "Fluorscopic" and insert --Fluoroscopic-- therefor In the Drawings Sheet 4 of 20, Fig. 3B, Reference Numeral 150, Line 2, Delete "TARET/TRAJECTORY" and insert --TARGET/TRAJECTORY-- therefor Signed and Sealed this
Tenth Day of October, 2023

Katherine Kelly Vidal
*Director of the United States Patent and Trademark Office*

CERTIFICATE OF CORRECTION (continued)
U.S. Pat. No. 11,707,363 B2

In the Specification

Column 13, Detailed Description of the Preferred Embodiments, Line 10, Delete "–50" and insert -- –5°-- therefor Column 13, Detailed Description of the Preferred Embodiments, Line 43, Delete "44." and insert --12.-- therefor Column 16, Detailed Description of the Preferred Embodiments, Line 46, Delete "44" and insert --12-- therefor Column 17, Detailed Description of the Preferred Embodiments, Line 23, Delete "154" and insert --160-- therefor Column 28, Detailed Description of the Preferred Embodiments, Line 51, Delete "306" and insert --326-- therefor Column 28, Detailed Description of the Preferred Embodiments, Line 53, Delete "322." and insert --321.-- therefor